(12) United States Patent
Faller et al.

(10) Patent No.: US 9,364,460 B2
(45) Date of Patent: Jun. 14, 2016

(54) PKC DELTA INHIBITORS FOR USE AS THERAPEUTICS

(71) Applicants: Douglas V. Faller, Weston, MA (US); Robert M. Williams, Fort Collins, CO (US)

(72) Inventors: Douglas V. Faller, Weston, MA (US); Robert M. Williams, Fort Collins, CO (US)

(*) Notice: Subject to any disclaimer, the term of this patent is extended or adjusted under 35 U.S.C. 154(b) by 0 days.

(21) Appl. No.: 14/428,232

(22) PCT Filed: Sep. 19, 2013

(86) PCT No.: PCT/US2013/060683
§ 371 (c)(1),
(2) Date: Mar. 13, 2015

(87) PCT Pub. No.: WO2014/047328
PCT Pub. Date: Mar. 27, 2014

(65) Prior Publication Data
US 2015/0283114 A1  Oct. 8, 2015

Related U.S. Application Data

(60) Provisional application No. 61/703,081, filed on Sep. 19, 2012.

(51) Int. Cl.
| | | |
|---|---|---|
| *C07D 209/86* | (2006.01) | |
| *C07D 405/06* | (2006.01) | |
| *A61K 31/404* | (2006.01) | |
| *A61K 31/403* | (2006.01) | |
| *C07D 487/14* | (2006.01) | |
| *A61K 45/06* | (2006.01) | |
| *A61K 31/06* | (2006.01) | |

(52) U.S. Cl.
CPC ............ *A61K 31/404* (2013.01); *A61K 31/403* (2013.01); *A61K 45/06* (2013.01); *C07D 209/86* (2013.01); *C07D 405/06* (2013.01); *C07D 487/14* (2013.01)

(58) Field of Classification Search
CPC ... A61K 31/404; A61K 45/06; A61K 31/403; C07D 209/86; C07D 405/06; C07D 487/14
See application file for complete search history.

(56) References Cited

U.S. PATENT DOCUMENTS

2011/0112182 A1* 5/2011 Kanthasamy ........ A61K 31/352
514/454
2012/0184517 A1* 7/2012 Marx ..................... A61K 31/00
514/171

OTHER PUBLICATIONS

Chen et al. "Protein kinase Cδ inactivation inhibits cellular proliferation and decreases survival in human neuroendocrine tumors" Endocrine-Related Cancer 2011, 18, 759-771.*
PCT Search and Patentability Report for PCT/US2013/060683, dated Apr. 15, 2014.
Chen, et al. "Protein kinase C delta inactivation inhibits cellular proliferation and decreases survival in human neuroendocrine tumors," Endocrine-related cancer (2011), 18, p. 759-771.
EP Search Report for Application No. 13839158.6, dated Jan. 13, 2016.

* cited by examiner

*Primary Examiner* — Nyeemah A Grazier
*Assistant Examiner* — Amanda L Aguirre
(74) *Attorney, Agent, or Firm* — Remenick PLLC

(57) ABSTRACT

The invention is directed to compounds that are specific inhibitors of PKC delta, and methods and compositions for the treatment and prevention of cancers and other disorders. Compositions comprising compounds of the invention are used to treat cancers such as, for example, carcinoid and neuroendocrine tumors, malignant melanomas, pancreatic, gastrointestinal and lung cancers. Neuroendocrine tumor cell lines of pulmonary and gastrointestinal origin are surprisingly sensitive to PKC delta inhibition by the compounds of the invention. The invention is further directed to methods, compositions and kits containing compounds of the formulas (Ia), (IIa), (IIIa), (IVa), and (V) as disclosed and described in FIGS. 11 and 12.

17 Claims, 17 Drawing Sheets

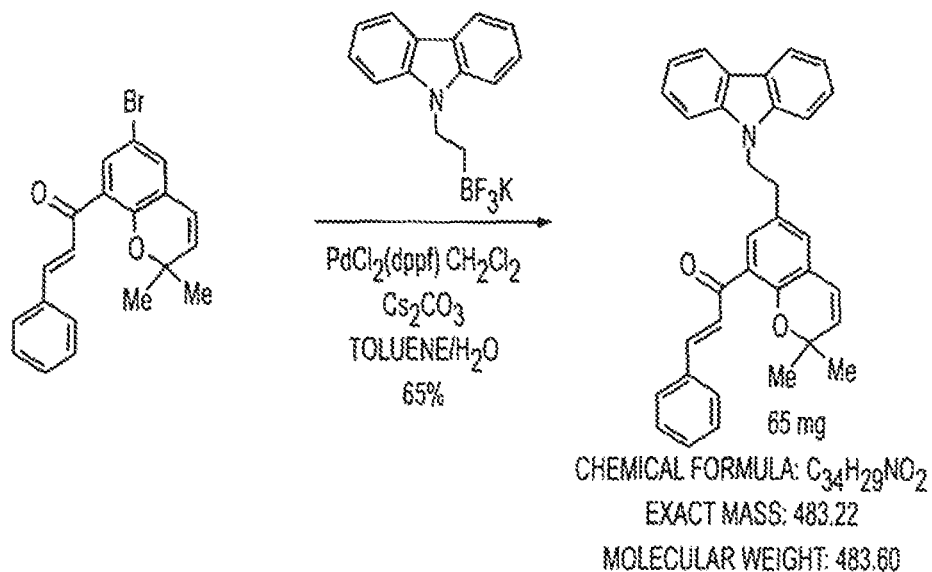
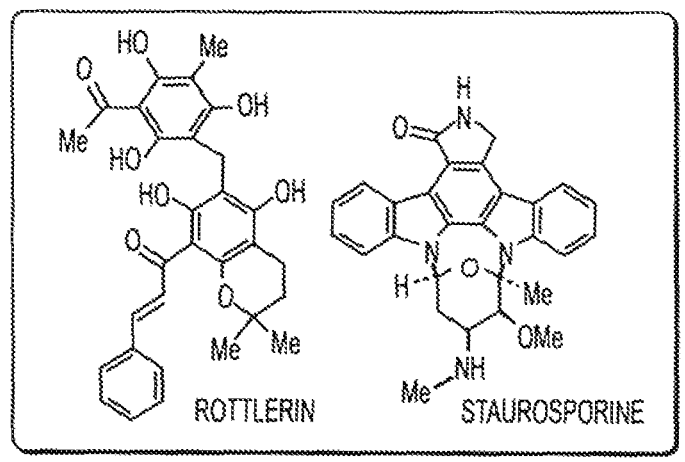
FIG. 5

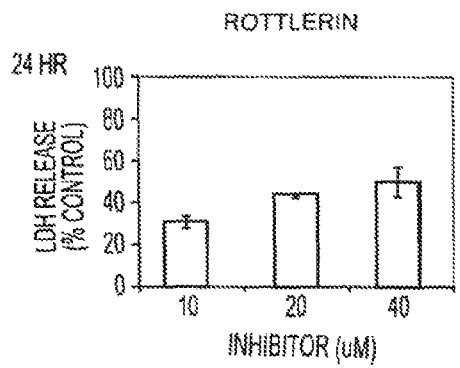
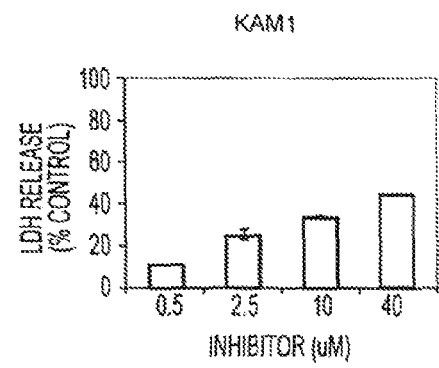
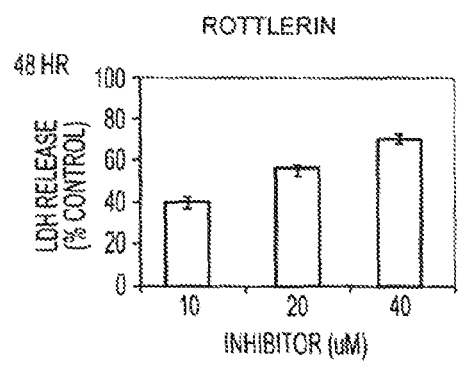
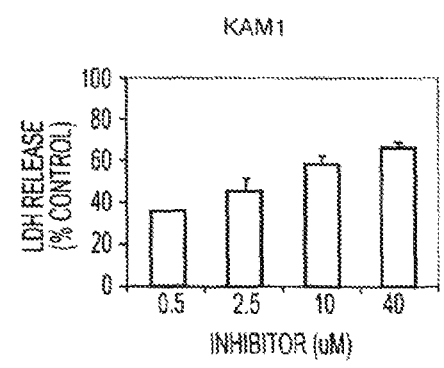
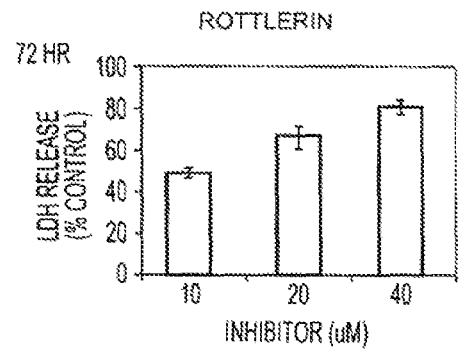
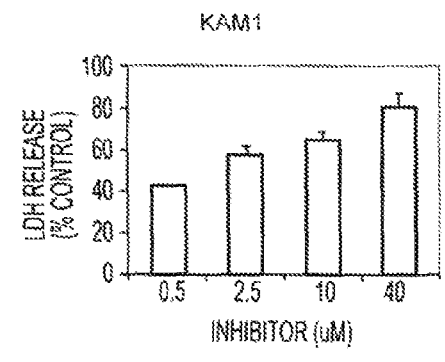
*FIG. 6A*                *FIG. 6B*

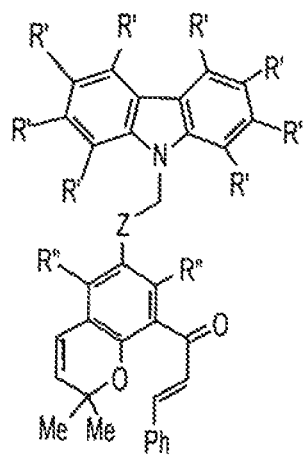
(Ia)
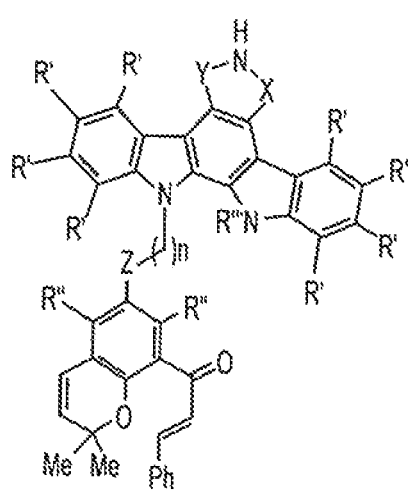
(IIa)
*FIG.12A*

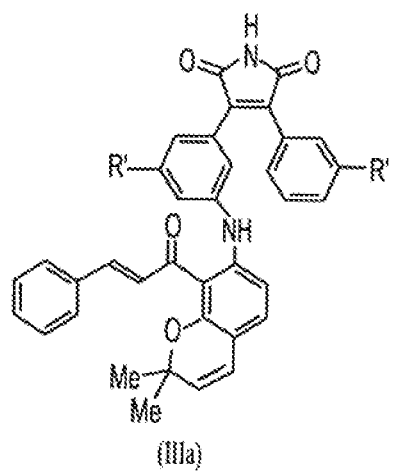
(IIIa)
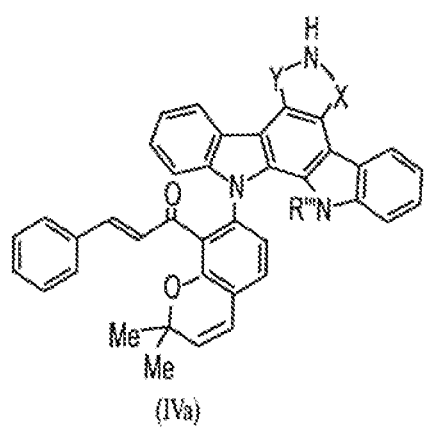
(IVa)
FIG. 12B (v)

WHEREIN:

$R_1$ = H, LOWER ALKYL, ⟋⟍Ar

Ar = ARYL $R_2$ AND $R_3$ CAN BE INDEPENDENTLY OR BOTH H; OH; OR

A, B, C, D = INDEPENDENTLY N OR CH

X, Y, Z, W = INDEPENDENTLY N OR CH

G = O, NR, S, $CH_2$

R = H, LOWER ALKYL, ARYL n = 0, 1, 2, 3, 4

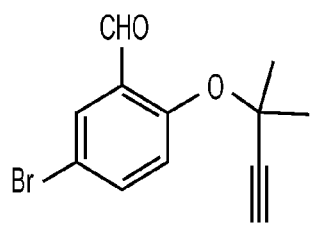
COMPOUND 2
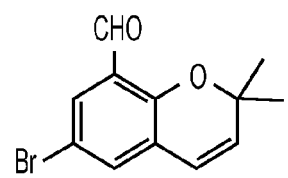
COMPOUND 3
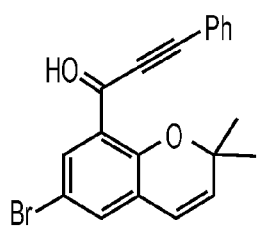
COMPOUND 4
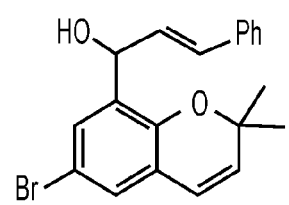
COMPOUND 5
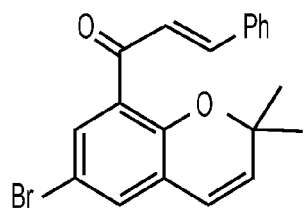
COMPOUND 6
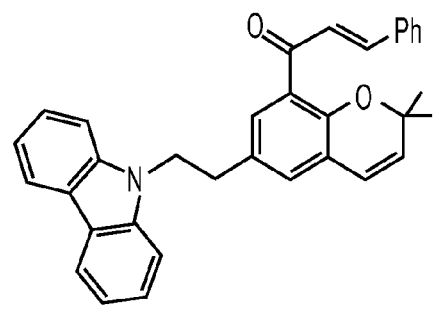
COMPOUND 8
*FIG. 12F*

PKC DELTA INHIBITORS FOR USE AS THERAPEUTICS

CROSS REFERENCE TO RELATED APPLICATIONS

This application is a National Stage submission under 35 U.S.C. §371 of International Application No. PCT/US2013/60683 filed Sep. 19, 2013, which claims priority to U.S. Provisional Application No. 61/703,081 filed Sep. 19, 2012, the entirety of which is incorporated by reference.

RIGHTS IN THE INVENTION

The invention was made with support from the U.S. Government under grant Nos. CA112102 and CA141908, awarded by the National Institutes of Health (NIH), and accordingly, the U.S. Government has certain rights in the invention.

BACKGROUND

1. Field of the Invention

The invention is directed to compounds that are specific inhibitors of PKC delta, and, in particular, to methods and compositions as therapeutical treatments, and as diagnostics to treat or prevent disorders such as cancers.

2. Background of the Invention

Targeting cancer therapeutics towards specific mutations or abnormalities in tumor cells not found in normal tissues has the potential advantages of high selectivity for the tumor and correspondingly low secondary toxicities. At least 30% of all human malignancies display activating mutations in the RAS genes, and perhaps another 60% display other activating mutations in, or over-activity of, p21Ras signaling pathways. It was previously reported that aberrant activation of Ras produces an absolute dependency upon PKC delta-mediated survival pathways (Xia S, Forman L W, & Faller D V 2007 Protein Kinase C{delta} is required for survival of cells expressing activated p21RAS. *J Biol. Chem.* 282 13199-13210; Xia S, Chen Z, Forman L W, & Faller D V 2009 PKCdelta survival signaling in cells containing an activated p21Ras protein requires PDKI. *Cell Signal.* 21 502-508). Over-activity of p21Ras signaling therefore sensitizes tumor cells to apoptosis induced by suppression of PKC delta, whereas suppression of PKC delta is not toxic to cells with normal levels of p21Ras activity or signaling (Chen C Y & Faller D V 1995 Direction of p21Ras-generated signals towards cell growth or apoptosis is determined by protein kinase C and Bcl-2. Oncogene 111487-1498; Xia S, Forman L W, & Faller D V 2007 Protein Kinase C{delta} is required for survival of cells expressing activated p21RAS. *J Biol. Chem.* 282 13199-13210; Chen C Y & Faller D V 1996 Phosphorylation of Bcl-2 protein and association with p21 (Ras) in Ras-induced apoptosis. *J. Biol. Chem.* 271 2376-2379; Chen C Y, Liou J, Forman L W, & Faller D V 1998a Correlation of genetic instability and apoptosis in the presence of oncogenic Ki-Ras. *Cell Death Differentiation.* 5 984-995; Chen C Y, Liou J, Forman L W, & Faller D V 1998b Differential regulation of discrete apoptotic pathways by Ras. *J. Biol. Chem.* 273 16700-16709; Chen C Y, Juo P, Liou J, Yu Q, Blenis J, & Faller D V 2001 Activation of FADD and Caspase 8 in Ras-mediated apoptosis. *Cell Growth Differ.* 12 297-306; Liou J S, Chen C Y, Chen J S, & Faller D V 2000 Oncogenic Ras mediates apoptosis in response to protein kinase C inhibition through the generation of reactive oxygen species. *J. Biol. Chem.* 275 39001-39011; Liou J S, Chen J-C, & Faller D V 2004 Characterization of p21Ras-mediated apoptosis induced by Protein Kinase C inhibition and application to human tumor cell lines. *J. Cell Physiol.* 198 277-294). This tumor-susceptibility designated "Ras-mediated apoptosis" can be exploited for specific targeted cancer therapeutics.

Bronchopulmonary, gastrointestinal and pancreatic neuroendocrine tumors are rare tumors originating from neuroendocrine tissues (Oberg K 1999 Neuroendocrine gastrointestinal tumors—a condensed overview of diagnosis and treatment. *Ann. Oneal.* 10 Suppl 2:S3-8. S3-S8). Clinical symptoms are often caused by the production of hormonally-active substances by the tumor such as serotonin, gastrin, insulin, vasoactive intestinal peptide, pancreatic polypeptide, or substanceP. Chromogranin A is produced by 80-100% of neuroendocrine tumors and serves as a reliable biochemical marker. The disease can be cured by early surgery, but the vast majority of tumors have metastases at the time of diagnosis, which makes palliation the cornerstone of management. Debulking surgery, liver artery embolization, and chemotherapy aim at tumor mass reduction, whereas somatostatin analogues and IFN are used for control of symptoms (Arnold R, Simon B, & Wied M 2000 Treatment of neuroendocrine GEP tumours with somatostatin analogues: a review. *Digestion.* 62 Suppl1 84-91; Frank M, Klose K J, Wied M, Ishaque N, Schade-Brittinger C, & Arnold R 1999 Combination therapy with octreotide and alpha-interferon: effect on tumor growth in metastatic endocrine gastroenteropancreatic tumors. *Am. J. Gastroenterol.* 94 1381-1387). Radioactively-labeled somatostatin analogues have been used in trials, with response rates 30% (Arnold R, Wied M, & Behr T H 2002 Somatostatin analogues in the treatment of endocrine tumors of the gastrointestinal tract. *Expert. Opin. Pharmacother.* 3 643-656).

Response rates of cytoreductive approaches to such cancers are generally below 60%, however, and their use has limited utility because long-term responses are not maintained (Oberg K 2001 Chemotherapy and biotherapy in the treatment of neuroendocrine tumours. *Ann. Oncol.* 12 Suppl2: S111-4.). Accordingly, new and more effective approaches are therefore needed in the treatment of neuroendocrine malignancies.

Carcinoid and other neuroendocrine tumors of the gastrointestinal tract share a number of the same genetic abnormalities (deletions and mutations) as adenocarcinomas (Leotlela P D, Jauch A, Holtgreve-Grez H, & Thakker R V 2003 Genetics of neuroendocrine and carcinoid tumours. *Endocr. Relat Cancer.* 10 437-450; Leotlela et al. 2003; Arber N, Neugut A I, Weinstein I B, & Holt P 1997 Molecular genetics of small bowel cancer. *Cancer Epidemiol. Biomarkers Prev.* 6 745-748). These abnormalities include activation of Ras directly by mutations, indirectly by loss of Ras-regulatory proteins such as NF-1, or via constitutive activation of downstream effector pathways of Ras, such as PI$_3$K and Raf/MAP kinase. For example, activation of H-Ras and Ki-Ras are detected in a significant fraction of carcinoid and other gastrointestinal tumors (65% and 10%, respectively) (Liedke M, Karnbach C, Kalinin V, Herbst B, Frilling A, & Broelsch C E 1998 [Detection of H-ras and K-ras in tumors of gastrointestinal-pancreatic system]. *Langenbecks Arch. Chir Suppl Kongressbd.* 115 255-259; Maitra A, Krueger J E, Tascilar M, Offerhaus G J, Angeles-Angeles A, Klimstra D S, Hruban R H, & Albores-Saavedra J 2000 Carcinoid tumors of the extrahepatic bile ducts: a study of seven cases. *Am. J. Surg. Pathol.* 24 1501-1510). Ras can also be activated in carcinoid and other neuroendocrine by either point mutation or loss of regulators of Ras, such as RassF1A or NF-1 (Liu L, Broaddus R R, Yao J C, Xie S, White J A, Wu T T, Hamilton S R, & Rashid A 2005 Epigenetic alterations in neuroendocrine tumors: methylation of RAS-association domain family 1, isoform A and p16 genes are associated with metastasis. *Mod. Pathol.* 18 1632-1640; Stancu M, Wu T T, Wallace C, Houlihan P S, Hamilton S R, & Rashid A 2003; Genetic alterations in goblet cell carcinoids of the vermiform appendix and comparison with gastrointestinal carcinoid tumors. *Mod. Pathol.* 16 1189-1198; Bausch B, Borozdin W, Mautner V F, Hoffmann M M, Boehm D, Robledo M, Cascon A, Harenberg T, Schiavi F, Pawlu C, et al. 2007 *Germline NF*1 mutational spectra and loss-of-heterozygosity analyses in patients with pheochromocytoma and neurofibromatosis type 1. *J. Clin. Endocrinol. Metab.* 92 2784-2792). The Raf/mitogen-activated protein kinase (Raf/MAP kinase), or the MAP kinases directly downstream of Raf, are frequently activated in carcinoid tumors (Tannapfel A, Vomschloss S, Karhoff D, Markwarth A, Hengge U R, Wittekind C, Arnold R, & Horsch D 2005 BRAF gene mutations are rare events in gastroenteropancreatic neuroendocrine tumors. *Am. J. Clin. Pathol.* 123 256-260; Karhoff D, SauerS, Schrader J, Arnold R, Fendrich V, Bartsch D K, & Horsch D 2007 Rap1/B-Raf signaling is activated in neuroendocrine tumors of the digestive tract and Raf kinase inhibition constitutes a putative therapeutic target. *Neuroendocrinology* 85 45-53; Perren A, Schmid S, Locher T, Saremaslani P, Bonvin C, Heitz P U, & Komminoth P 2004 BRAF and endocrine tumors: mutations are frequent in papillary thyroid carcinomas, rare in endocrine tumors of the gastrointestinal tract and not detected in other endocrine tumors. *Endocr. Relat Cancer* 11 855-860; Kunnimalaiyaan M & Chen H 2006 The Raf-1 pathway: a molecular target for treatment of select neuroendocrine tumors? *Anticancer Drugs* 17 139-142). The PI₃K pathway is activated in carcinoid tumors from deletion of the tumor suppressor gene PTEN (phosphatase and tensin homologue). Loss of PTEN in neuroendocrine and carcinoid tumors, increases in frequency with the loss of differentiation in the tumor (Wang G G, Yao J C, Worah S, White J A, Luna R, Wu T T, Hamilton S R, & Rashid A 2005 Comparison of genetic alterations in neuroendocrine tumors: frequent loss of chromosome 18 in ileal carcinoid tumors. *Mod. Pathol.* 18 1079-1087), and loss of PTEN expression may represent an important step in the progression of neuroendocrine tumors (Wang L, Ignat A, & Axiotis C A 2002 Differential expression of the PTEN tumor suppressor protein in fetal and adult neuroendocrine tissues and tumors: progressive loss of PTEN expression in poorly differentiated neuroendocrine neoplasms. *Appl. Immunohistochem. Mol. Morphol.* 10 139-146).

Gastrointestinal and pulmonary carcinoid tumors are uncommon, but unfortunately are generally refractory to conventional cytotoxic chemotherapeutic and radiotherapeutic approaches. Many targeted therapeutic approach such as induction of Ras-mediated apoptosis by PKC delta inhibition, which selectively takes advantage of the very oncogenic mutations which contribute to the malignancy of the tumor, may have potential as a novel and selective therapeutic modality for these malignancies.

SUMMARY OF THE INVENTION

The present invention generally relates to compounds which were discovered to be specific inhibitors of PKC delta, and methods and compositions thereof. In some embodiments, compositions comprising these compounds can be used in a method to treat cancers, e.g., carcinoid and neuroendocrine tumors, malignant melanomas, pancreatic, gastrointestinal and lung cancers. Herein, the inventors have demonstrated that human neuroendocrine tumor cell lines of pulmonary and gastrointestinal origin are surprisingly sensitive to PKC delta inhibition using the compounds as disclosed herein (Chen, Z., Forman, L. W., Miller, K. A., English, B., Takashima, A., Bohacek, R. A., Williams, R. M., and Faller, D. V.: The proliferation and survival of human neuroendocrine tumors is dependent upon protein kinase C-delta. 2011, *Endocrine-Related Cancers*, 18:759-71).

In certain embodiments, a PKC delta inhibitory compound for use in the methods, compositions and kits as disclosed herein is of the formula (Ia), (IIa), (IIIa), (IVa), or (V) (see FIG. 12).

The compounds of the invention specifically inhibit PKC delta.

The invention also provides pharmaceutical compositions comprising a therapeutically effective amount of a compound of the invention and a pharmaceutically acceptable excipient.

Herein the inventors have demonstrated that a compound as disclosed herein is a specific inhibitor of PKC delta and produces a dose-dependent and time-dependent decrease in cell numbers for a number of neuroendocrine tumor cell lines: BON1 (foregut carcinoid tumor cell line), CNDT 2.5 and H727 cell lines. Additionally, the inventors have demonstrated that the compounds as disclosed herein significantly suppress cell growth and clonogenic capacity of these cell lines.

Accordingly, one aspect of the present invention relates to use of a compound of formula Ia), (IIa), (IIIa), (IVa), or (V) and its derivatives and analogues in a method to treat cancers and/or inhibit cell proliferation, for example, bronchopulmonary, gastrointestinal and pancreatic neuroendocrine tumors, malignant melanomas, pancreatic, gastrointestinal and lung cancers.

Other aspects of the proposed invention relate to methods to treat human neuroendocrine Tumors. In particular, the inventors have demonstrated that inhibition or downregulation of PKC delta by siRNA, and small molecule inhibitors such as a compound of formula (Ia), (IIa), (IIIa), (IVa), or (V) can efficiently and selectively repress the growth of human neuroendocrine cells, derived from bronchopulmonary, foregut and hindgut tumors carcinoid and neuroendocrine tumors malignant melanomas, pancreatic, gastrointestinal and lung cancers.

Accordingly, in some embodiments a pharmaceutical composition comprising at least compound as disclosed herein can be used in a method to treat a cancer in a subject. In some embodiments, a compound as disclosed herein can be used in a method to treat a cancer in a subject for example, a bronchopulmonary cancer, a gastrointestinal cancer or a pancreatic neuroendocrine cancer, carcinoid and neuroendocrine tumors, malignant melanomas, pancreatic, gastrointestinal and lung cancers. In some embodiments, a compound as disclosed herein can be used in a method to treat a carcinoid and/or neuroendocrine cancer. In some embodiments, a neuroendocrine cancer can be derived from a bronchopulmonary, or foregut or hindgut tumor.

In another embodiment, the present invention can be used as a method of treating a pathological condition in a subject that is responsive to inhibition of PKC delta, comprising administering to the subject a therapeutically or prophylactically effective amount of a compound, or a pharmaceutical composition thereof. In certain embodiments, the compound or pharmaceutical composition is administered orally. In other embodiments, the compound or pharmaceutical composition is administered parenterally (e.g., intravenously).

The compounds of the invention can also be used in a method of inhibiting PKC delta in a subject and a method of treating a subject with cancer, for example, a bronchopulmonary cancer, a gastrointestinal cancer or a pancreatic neuroendocrine cancer, malignant melanomas, pancreatic, gastrointestinal and lung cancers in which a therapeutically effective amount of an inventive compound, or a pharmaceutical composition thereof, is administered to the subject.

The invention further relates to the use of the compounds of the invention for the manufacture of a medicament for treating pathological conditions responsive to inhibition of PKC delta for treating a subject with cancer, for example, a bronchopulmonary cancer, a gastrointestinal cancer or a pancreatic neuroendocrine cancer, malignant melanomas, pancreatic, gastrointestinal and lung cancers.

Other embodiments and advantages of the invention are set forth in part in the description, which follows, and in part, may be obvious from this description, or may be learned from the practice of the invention.

DESCRIPTION OF THE DRAWINGS

This patent or application contains at least one drawing executed in color. Copies of this patent or patent application with color drawing(s) will be provided by the Office upon request and payment of the necessary fee.

(FIG. 1C) Immunoblot analyses show down-regulation of PKC delta 72 hr after treatment with lentivirus-transfected PKC delta-targeting siRNA versus scrambled siRNA-treated controls. Lentiviral PKC delta-targeting siRNA inhibited PKC delta protein expression, as determined by immunoblotting.

(FIG. 2D) Immunoblot analyses of PKC delta protein 72 hr after exposure to lentivirus-transfected PKC delta-targeting shRNA compared to infection with lentivirus containing a scrambled shRNA-treated (Sc-shRNA), or mock-infected controls.

FIG. 5 illustrates the structure of KAM1, a rottlerin/staurosporine chimera.

FIG. 6. Cytotoxic effects of PKCδ inhibitors on human neuroendocrine tumor cell lines. H727 cells were grown to 50% confluence in 96-well plates and then exposed to Rottlerin (panel A) or KAM1 (panel B) at the concentrations indicated. Cells exposed to vehicle alone served as controls. After 24, 48 and 72 hours of treatment, cell cytotoxicity was evaluated by LDH-release assay. Baseline LDH release (vehicle treatment) values were subtracted at each time point. Total maximal LDH release is assigned the arbitrary value of 100%. Error bars represent SEM. P values for comparison between control (vehicle) and Rottlerin or KAM1 effects on LDH release reached significance by 24 hr of exposure (p≤0.003), and remained significant at the 48 and 72 hr time points.

FIG. 10A illustrates p21Ras activity in neuroendocrine tumor cell lines. Nuclear-free lysates containing a total of 400 µg of protein from each indicated cell type were used for analysis of Ras activity by Raf-RBD pull-down of GTP-bound p21Ras. Equal loading was demonstrated by re-probing the blot with anti-β-actin antibody. Pan-p21Ras protein expression levels were also analyzed. Lanes 1-5 represent lysates from: NIH/3T3 (negative control), NIH/3T3-Ras (positive control), BON1, H727, and CNDT cells, respectively. FIG. 10B illustrates the activation of Ras signaling pathways in neuroendocrine tumor cell lines. Cell lysates from negative control MCFIO cells (lane 1); positive control MCF-10-Ras cells (lane 2); BON1 cells (lane 3); H727 cells (lane 4); and CNDT cells (lane 5) were separated by SDS-polyacrylamide gel electrophoresis, transferred to a membrane, and immunoblotted with antibodies against ERK, phospho-ERK, AKT, phospho-Thr308 AKT, and GAPDH (as a loading control).

FIGS. 12A-D) and F show preferential embodiments of compounds for the methods and composition of the invention.

DESCRIPTION OF THE INVENTION

Figure 1A:
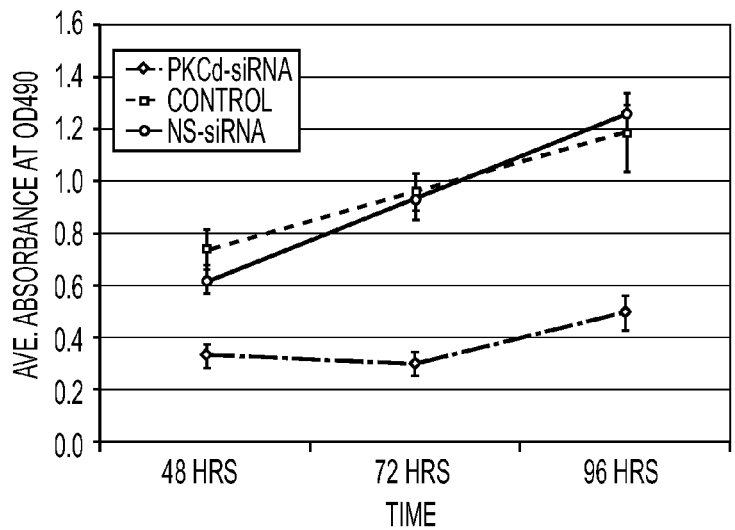
FIGS. 1A-1C. Effects of PKC delta knockdown by SiRNA on proliferation of human neuroendocrine tumor BON1 and CNDT cells. BON1 (FIG. 1A) and CNDT 2.5 (FIG. 1B) cells were grown to 50% confluence in 96-well plates and then treated with PKC delta-siRNA or scrambled siRNA (sc-siRNA). The corresponding solvent equivalent volumes were used as vehicle controls (Control). After 48, 72, and 96 hours of treatment, cell number was evaluated by MTS assay.

As discussed above, there remains a need for treatment of malignancies. The present invention provides compounds of general formulae (Ia), (IIa), (IIIa), (IVa), and (V) which are useful as inhibitors of PKC delta, and thus are useful for the treatment of diseases or disorders associated with increased activity of PKC delta, and/or increased or overexpression of PKC delta. In certain embodiments, the inventive compounds are useful in the treatment of cancer in a subject, for example, a bronchopulmonary cancer, a gastrointestinal cancer or a pancreatic neuroendocrine cancer. In some embodiments, the cancer is a carcinoid and/or neuroendocrine cancer, malignant melanoma, pancreatic, gastrointestinal or lung cancer. In some embodiments, a neuroendocrine cancer is of pulmonary and gastrointestinal origin, for example, a cancer is derived from a bronchopulmonary, or foregut or hindgut tumor.

Definitions

Before further description of the present invention, and in order that the invention may be more readily understood, certain terms are first defined and collected here for convenience.

Certain compounds of the present invention, and definitions of specific functional groups are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group," has used herein, it is meant that a particular functional moiety, e.g., C, O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group must be selectively removed in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference. Furthermore, a variety of carbon protecting groups are described in Myers, A.; Kung, D. W.; Zhong, B.; Movassaghi, M.; Kwon, S. *J. Am. Chem. Soc.* 1999, 121, 8401-8402, the entire contents of which are hereby incorporated by reference.

The term "PKC delta" is used interchangeably herein with PCK delta or PKC-δ, and refers to the amino acid sequences of substantially purified PKC delta obtained from any species, particularly mammalian, including bovine, ovine, porcine, murine, equine, and preferably human, from any source whether natural, synthetic, semi-synthetic, or recombinant. PKC delta (also known in the art as aliases: PRKCD; MAY 1; MGC49908; nPKCdelta) is a member of the PKC family.

The term "inhibitor" or "antagonist", as used herein in reference to a PKC delta antagonist or inhibitor, refers to a molecule which, when bound to PKC delta, decreases the amount or the duration of the effect of the biological or immunological activity of PKC delta, regardless of whether the inhibitor functions indirectly or directly on PKC delta.

The term "PKC delta inhibitor" or "PKC delta antagonist" as used herein refers to an agent that reduces or attenuates the biological activity of the PKC delta polypeptide in a cell, either by decreasing the activity of the PKC delta polypeptide or by effectively reducing the amount of PKC delta polypeptide in a cell or by decreasing the enzymatic activity of the PKC delta polypeptide. A "PKC delta inhibitor" thus refers to a molecule having the ability to inhibit a biological function of a native PKC delta, as well as a mutant PKC delta protein. Compounds that are PKC delta include all solvates, hydrates, pharmaceutically acceptable salts, tautomers, stereoisomers, and prodrugs of the compounds. While preferred PKC delta herein specifically interact with, e.g. bind to, a PKC delta, molecules that inhibit PKC delta biological activity by interacting with other members of the PKC delta signal transduction pathway are also specifically included within this definition. Useful PKC delta inhibitors may selectively inhibit PKC delta, may selectively inhibit calcium-independent or novel PKC isoforms. A preferred PKC delta biological activity inhibited by a PKC delta inhibitor as disclosed herein is associated with the development, growth, or spread of a tumor or associated with the development or proliferation. Some PKC delta inhibitors may function by more than one mechanism to inhibit overall PKC delta activity in a cell.

The term a "selective" PKC delta inhibitor as used herein refers to an agent that inhibits PKC delta activity with a Ki at least 10-fold less, preferably, at least 100-fold less, than the Ki for inhibition of one or more other PKC isoforms (e.g., PKC α, PKC β and PKC γ or any other).

A "PKC delta targeting treatment" is the use of one or more PKC delta inhibitors to therapeutically reduce PKC delta activity in a cell. A PKC delta inhibitors may preferably be agents that selectively inhibit PKC delta. As used herein, an agent that "selectively inhibits" PKC delta means an agent that reduces the activity of PKCdelta more than it reduces the activity of one or more other PKC isoforms.

The term "decreased PKC delta activity" means a substantial decrease by a statistically significant amount in the total PKC delta polypeptide activity of the PKC delta enzyme as a result of inhibition with a PKC delta inhibitor compound as disclosed herein as compared to in the absence of such inhibitor.

The term "biologically active", as used herein, refers to a protein having structural, regulatory, or biochemical functions of a naturally occurring molecule, and displays the activity of the molecule in a cellular and/or in vivo assay.

The terms "Ras" and "p21Ras" are used interchangeably herein to refer to the protein product of a Ras gene. The mammalian ras gene family consists of the Harvey and Kirsten ras genes (c-Hras1 and c-Kras2), an inactive pseudo gene of each (c-Hras2 and c-K-ras1) and the N-ras gene. The p21Ras protein products of the three ras genes (p21HRas, p21KRas and p21NRas, respectively) differ significantly only in their C-terminal 40 amino acids, and each are activated by the same or corresponding activating mutations. The three ras gene sequences, as well as their protein products, for a variety of animals, (e.g. mammals, including humans) are well known in the field. Examples of each of the human ras gene coding sequences are provided in International Application W0/20071106424 (see FIG. 8: H-ras in FIG. 8A, K-ras in FIG. 8B, and N-ras in FIG. 8C), which is incorporated herein in its entirety by reference.

As used herein, the term "activated Ras mutation" refers to the presence of a genomic mutation in a ras gene which leads to the expression of an activated form of the Ras protein. The term "wild-type" is used herein to refer to nucleic acids encoding Ras proteins that do not contain activating mutations, and also to refer to Ras proteins which do not result from activating mutations.

The term "aberrantly increased Ras signaling" as used herein refers to a statistically significant increase in Ras signaling in one or more cells (e.g. tumor or pre-tumor cells) as measured by a determination of the percentage of Ras in the activated state and/or activity or one or more downstream effectors of Ras. Such determination is further made by comparison of similar measurements made in a similar cells type under appropriate conditions. Increased activity may be surmised by detection of a known activated Ras mutant, at the nucleic acid or the protein level. Increased activity of Ras may also be surmised by a detected abnormal increase in the activity and/or presence of a known activator of Ras or abnormal decrease in known deactivator of Ras, as described herein. Verification of actual increase in Ras signaling may be used to confirm such surmisal.

As used herein, the term "subject" or "patient" refers to any mammal. The subject is preferably human, but can also be a mammal in need of veterinary treatment, e.g. domestic animals, farm animals, and laboratory animals. For example, the subject may be a subject diagnosed with a benign or malignant tumor, a cancer or a hyperplasia. The subject may be a cancer patient who is receiving treatment modalities against cancer or has undergone a regimen of treatment, e.g., chemotherapy, radiation and/or surgery. The subject may be a cancer patient whose cancer appears to be regressing.

As used herein, the phrase "expression" is used to refer to the transcription of a gene product into mRNA (gene expression) and is also used to refer to the expression of the protein encoded by the gene.

As used herein the term "over-expression" is used to refer to increased production of a specific mRNA and/or protein in a cell, wherein the actual mRNA and protein product do not contain activating mutations. As used herein, the term "over-activation", as used to refer to Ras or an upstream or downstream effector, is used to refer to increased signaling through an otherwise non-activated form of a pathway member. Over-activation of a molecule typically results from increased activation (e.g. upstream signaling) or decreased de-activation (e.g. downstream negative regulation) of the molecule. Over-activation and over-expression of a specific gene/protein can co-exist, and often the existence of one contributes to the existence of the other in a cell.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents. Furthermore, therapeutically effective amounts will vary, as recognized by those skilled in the art, depending on the specific disease treated, the route of administration, the excipient selected, and the possibility of combination therapy. A physiological effect of a compound as disclosed herein on the subject can be measured to determine the therapeutically effective amount include, without limitation, decreased proliferation in a subject and the like.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds.

Combinations of substituents and variables envisioned by this invention are preferably those that result in the formation of stable compounds useful in the treatment, for example of proliferative disorders, including, but not limited to cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, and alkynyl moieties. Thus, as used herein, the term "alkyl" includes straight and branched alkyl groups. An analogous convention applies to other generic terms such as "alkenyl", "alkynyl", and the like.

Furthermore, as used herein, the terms "alkyl", "alkenyl", "alkynyl", and the like encompass both substituted and unsubstituted groups. In certain embodiments, as used herein, "lower alkyl" is used to indicate those alkyl groups (substituted, unsubstituted, branched or unbranched) having 1-6 carbon atoms.

The term "alkyl" is a saturated hydrocarbon in a molecule that is bonded to one other group in the molecule through a single covalent bond from one of its carbon atoms. Alkyl groups can be cyclic or acyclic, branched or unbranched (straight chained) and substituted or unsubstituted when straight chained or branched. An alkyl group typically has from 1 to about 12 carbon atoms, for example, one to about six carbon atoms or one to about four carbon atoms. Lower alkyl groups have one to four carbon atoms and include methyl, ethyl, n-propyl, iso-propyl, n-butyl, sec-butyl and tert-butyl. When cyclic, an alkyl group typically contains from about 3 to about 10 carbons, for example, from about 3 to about 8 carbon atoms, e.g., a cyclopropyl group, a cyclobutyl group, a cyclopentyl group, a cyclohexyl group, a cycloheptyl group or a cyclooctyl group.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties, and the like, which again, may bear one or more substituents. Alkenyl groups include, but are not limited to, for example, ethenyl, propenyl, butenyl, 1-methyl-2-buten-1-yl, and the like.

Representative alkynyl groups include, but are not limited to, ethynyl, 2-propynyl (propargyl), 1-propynyl, and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH₂-cyclopropyl, cyclobutyl, —CH₂-cyclobutyl, cyclopentyl, —CH₂-cyclopentyl, cyclohexyl, —CH₂-cyclohexyl, cyclohexenylethyl, cyclohexanylethyl, norborbyl moieties, and the like, which may bear one or more substituents.

The term "alkoxy" or "alkyloxyl" or "thioalkyl", as used herein, refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl group contains 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include, but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure $NH_2R'$—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl contains 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino, n-propylamino, and the like.

Some examples of substituents of the above-described aliphatic (and other) moieties of compounds of the invention include, but are not limited to, aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; —F; —Cl; —Br; —I; —OH; —NO₂; —CN; —CF₃; —CH₂CF₃; —CHCl₂; —CH₂OH; —CH₂CH₂OH; —CH₂NH₂; —CH₂SO₂CH₃; —C(O)$R_x$; —CO₂($R_x$); —CON($R_x$)₂; —OC(O)$R_x$; —OCO₂$R_x$; —OCON($R_x$)₂; —N($R_x$)₂; —S(O)₂$R_x$; —N$R_x$(CO)$R_x$; wherein each occurrence of $R_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2), wherein n is an integer. A mono- or polycyclic, unsaturated moiety that does not satisfy one or all of these criteria for aromaticity is defined herein as "non-aromatic," and is encompassed by the term "alicyclic."

In general, the term "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S, and N within the ring (i.e., in place of a ring carbon atom). In certain embodiments, the term "heteroaromatic moiety" refers to a planar ring comprising at least on heteroatom, having p-orbitals perpendicular to the plane of the ring at each ring atom, and satisfying the Huckel rule where the number of pi electrons in the ring is (4n+2), wherein n is an integer.

It will also be appreciated that aromatic and heteroaromatic moieties, as defined herein may be attached via an alkyl or heteroalkyl moiety and thus also include -(alkyl)aromatic, -(heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl, and the like.

The term "heteroaryl", as used herein, does not differ significantly from the common meaning of the term in the art, and refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; —F; —Cl; —Br, —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; and —NR$_x$(CO)R$_x$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or (alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "cycloalkyl", as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl, and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; —F; —Cl; —Br, —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described herein may be substituted or unsubstituted. Additional examples of generally applicable substituents are illustrated by the specific embodiments described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to, aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; —F; —Cl; —Br, —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; and —NR$_x$(CO)R$_x$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described herein may be substituted or unsubstituted. Additional examples of generally applicable substituents are illustrated by the specific embodiments described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S, and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6-, or 7-membered ring or a polycyclic group wherein at least one ring atom is a heteroatom selected from O, S, and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroaryloxy; heteroaryloxy; alkylthio; arylthio; heteroalkylthio; heteroarylthio; F; Cl; Br, I; —OH; $NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$; wherein each occurrence of $R_x$ independently includes, but is not limited to, aliphatic, alicyclic; heteroaliphatic, heterocyclic, aromatic, heteroaromatic, aryl, heteroaryl, alkylaryl, alkylheteroaryl, heteroalkylaryl, or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, or heteroaryl substituents described herein may be substituted or unsubstituted. Additional examples or generally applicable substituents are illustrated by the specific embodiments described herein.

Additionally, it will be appreciated that any of the alicyclic or heterocyclic moieties described herein may comprise an aryl or heteroaryl moiety fused thereto. Additional examples of generally applicable substituents are illustrated by the specific embodiments described herein. The term "acyl", as used herein, refers to a carbonyl-containing functionality, e.g., —C(O)R, wherein R is an aliphatic, alycyclic, heteroaliphatic, heterocyclic, aryl, heteroaryl, (aliphatic)aryl, (heteroaliphatic)aryl, heteroaliphatic(aryl), or heteroaliphatic(heteroaryl) moiety, whereby each of the aliphatic, heteroaliphatic, aryl, or heteroaryl moieties is substituted or unsubstituted, or is a substituted (e.g., hydrogen or aliphatic, heteroaliphatic, aryl, or heteroaryl moieties) oxygen or nitrogen containing functionality (e.g., forming a carboxylic acid, ester, or amide functionality).

Acyl groups can be hydrolyzed or cleaved from a compound by enzymes, acids, or bases. One or more of the hydrogen atoms of an acyl group can be substituted, as described below. Typically, an acyl group is removed before a compound of the present invention binds to a metal ion such as iron (III).

Suitable substituents for alkyl and acyl groups include —OH, —O(R"), —COOH, =O, —$NH_2$, —NH(R"), —$NO_2$, —COO(R"), —$CONH_2$, —CONH(R"), —$CON(R")_2$, and guanidine. Each R" is independently an alkyl group or an aryl group. These groups can additionally be substituted by an aryl group (e.g., an alkyl group can be substituted with an aromatic group to form an arylalkyl group). A substituted alkyl or acyl group can have more than one substituent.

Aryl groups include carbocyclic aromatic groups such as phenyl, p-tolyl, 1-naphthyl, 2-naphthyl, 1-anthracyl and 2-anthracyl. Aryl groups also include heteroaromatic groups such as N-imidazolyl, 2-imidazolyl, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl.

Aryl groups also include fused polycyclic aromatic ring systems in which a carbocyclic, alicyclic, or aromatic ring or heteroaryl ring is fused to one or more other heteroaryl or aryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazolyl, 2-benzoxazolyl, 2-benzimidazolyl, 1-isoquinolinyl, 3-isoquinolinyl, 1-isoindolyl and 3-isoindolyl.

The term "O-protecting group" means a substituent which protects hydroxyl groups against undesirable reactions during synthetic procedures. Examples of O-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates.

The term "leaving group" refers to a molecular fragment that can departs with a pair of electrons in heterolytic bond cleavage. Examples of leaving groups include, but are not limited to, halides, such as F, Br, Cl, I; sulfonates, such as tosylates, nosylates, myselates; nonaflates; triflates; fluorosulfonates; nitrates; and phosphates.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like. In certain embodiments, the alkyl group is perhalogenated (e.g., perfluorinated).

The term "amino", as used herein, refers to a primary (—$NH_2$), secondary (—$NHR_x$), tertiary (—$NR_xR_y$), or quaternary (—$N+R_xR_yR_z$) amine, where $R_x$, $R_y$, and $R_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "alkylidene", as used herein, refers to a substituted or unsubstituted, linear or branched saturated divalent radical of carbon and hydrogen atoms, having from one to n carbon atoms and having a free valence at both ends of the radical. The alkylidene moiety may be substituted.

The term "alkenylidene", as used herein, refers to a substituted or unsubstituted, linear or branched unsaturated divalent radical of carbon and hydrogen atoms, having from two to n carbon atoms and having a free valence at both ends of the radical, and wherein the unsaturation is present only as double bonds and wherein a double bond can exist between the first carbon of the chain and the rest of the molecule. The alkenylidene moiety may be substituted.

The term "alkynylidene", as used herein, refers to a substituted or unsubstituted, linear or branched unsaturated divalent radical of carbon and hydrogen atoms, having from two to n carbon atoms, having a free valence"—" at both ends of the radical, and wherein the unsaturation is present only as triple bonds and wherein a triple bond can exist between the first carbon of the chain and the rest of the molecule. The alkynylidene moiety may be substituted.

The term "carbamate", as used herein, refers to any carbamate derivative known to one of ordinary skill in the art. Examples of carbamates include t-Boc, Fmoc, benzyloxycarbonyl, alloc, methyl carbamate, ethyl carbamate, 9-(2-sulfo)fluorenylmethyl carbamate, 9-(2,7-dibromo)fluorenylmethyl carbamate, Tbfmoc, Climoc, Bimoc, DBD-Tmoc, Bimoc, Troc, Teoc, 2-phenylethyl carbamate, Adpoc, 2-chloroethyl carbamate, 1,1-dimethyl-2-haloethyl carbamate, DB-t-BOC, TCBOC, Bpoc, t-Bumeoc, Pyoc, Bnpeoc, N-(2-pivaloylamino)-1,1-dimethylethyl carbamate, NpSSPeoc. In certain embodiments, carbamates are used as nitrogen protecting groups.

Unless otherwise indicated, as used herein, the terms "alkyl", "alkenyl", "alkynyl", "heteroalkyl", "heteroalkenyl", "heteroalkynyl", "alkylidene", "alkynylidene", -(alkyl)aryl, -(heteroalkyl)aryl, -(heteroalkyl)aryl, -(heteroalkyl)heteroaryl, and the like encompass substituted and unsubstituted, and linear and branched groups. Similarly, the terms "aliphatic", "heteroaliphatic", and the like encompass substituted and unsubstituted, saturated and unsaturated, and linear and branched groups. Similarly, the terms "cycloalkyl", "heterocycle", "heterocyclic", and the like encompass substituted and unsubstituted, and saturated and unsaturated groups. Additionally, the terms "cycloalkenyl", "cycloalkynyl", "heterocycloalkenyl", "heterocycloalkynyl", "aromatic", "heteroaromatic", "aryl", "heteroaryl", and the like encompass both substituted and unsubstituted groups.

Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. The biological activity of pro-drugs may also be altered by appending functionality onto the compound, which may be catalyzed by an enzyme. Also, included are oxidation and reduction reactions, including enzyme-catalyzed oxidation and reduction reactions. Certain exemplary pharmaceutical compositions and pharmaceutically acceptable derivatives are discussed in more detail herein.

"Compound": The term "compound" or "chemical compound" as used herein can include organometallic compounds, organic compounds, metals, transitional metal complexes, and small molecules. In certain embodiments, polynucleotides are excluded from the definition of compounds. In other embodiments, polynucleotides and peptides are excluded from the definition of compounds. In certain embodiments, the term compound refers to small molecules (e.g., preferably, non-peptidic and non-oligomeric) and excludes peptides, polynucleotides, transition metal complexes, metals, and organometallic compounds.

"Small Molecule": As used herein, the term "small molecule" refers to a non-peptidic, non-oligomeric organic compound, either synthesized in the laboratory or found in nature. A small molecule is typically characterized in that it contains several carbon-carbon bonds, and has a molecular weight of less than 2000 g/mol, preferably less than 1500 g/mol, although this characterization is not intended to be limiting for the purposes of the present invention. Examples of "small molecules" that occur in nature include, but are not limited to, taxol, dynemicity and rapamycin, Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" *J. Am. Chem. Soc.* 1998, 120, 8565; incorporated herein by reference).

"Biological sample": As used herein the term "biological sample" includes, without limitation, cell cultures, or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g., blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g., fluid obtained from an abscess or any other site of infection or inflammation), or fluid obtained from a joint (e.g., a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue, or organ. Biological samples may also include sections of tissues such as frozen sections taken for histological purposes.

Biological samples also include mixtures of biological molecules including proteins, lipids, carbohydrates, and nucleic acids generated by partial or complete fractionation of cell or tissue homogenates. Although the sample is preferably taken from a human subject, biological samples may be from any animal, plant, bacteria, virus, yeast, etc.

"Pharmaceutically acceptable salt": As used herein, the term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts of amines, carboxylic acids, and other types of compounds, are well known in the art. For example, Berge et al. describe pharmaceutically acceptable salts in detail in *J. Pharmaceutical Sciences* 1977, 6, 1-19, incorporated herein by reference. The salts can be prepared in situ during the final isolation and purification of a compound of the invention, or separately by reacting a free base or free acid function with a suitable reagent, as described generally below. For example, a free base can be reacted with a suitable acid. Furthermore, where the compound of the invention carries an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid; or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level (e.g., in the absence of a compound of the invention).

The terms "increased", "increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level (e.g., in the absence of a compound of the invention).

The term "statistically significant" or "significantly" refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value.

The term "substantially" as used herein means a proportion of at least about 60%, or preferably at least about 70%, or at least about 80%, or at least about 90%, or at least about 95%, or at least about 97% or at least about 99% or more, or any integer between 70% and 100%.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N. Y., USA (1982); Sambrook et al., Molecular Cloning: A Laboratory Manual (2 ed.), Cold Spring Harbor Laboratory Press, Cold Spring Harbor, N. Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Compounds of the Invention

Compounds of this invention include those, as set forth above and described herein, and are illustrated in part by the various classes, subgenera, and species disclosed elsewhere herein. The present invention provides compounds that inhibit PKC delta, having the general formula (Ia), (IIa), (IIIa), (IVa), or (V), a set forth in FIGS. 11 A-M and 12 A-F inclusive.

In certain embodiments, the compound is of formula (Ia) wherein Z is $CH_2$, O, NH,S,C(R''')(R'''); each occurrence of R' is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $OR^B$; $-C(=O)R^B$; $-CO_2R^B$; $-C(=O)N(R^B)2$; $-CN$; $-SCN$; $-SR^B$; $-SOR^B$; $-SO_2R^B$; $-NO_2$; $-N(R^B)_2$; $-NHC(O)R^B$; or $-C(R^B)_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; or heteroarylthioxy; two R' can be taken together to form a fused cyclic group; each occurrence of R'' is independently hydrogen, halogen; cyclic, or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $OR^B$; $-C(=O)R^B$; $-CO_2R^B$; $-C(=O)N(R^B)_2$; $-CN$; $-SCN$; $-SR^B$; $-SOR^B$; $-SO_2R^B$; $-NO_2$; $-N(R^B)_2$; $-NHC(O)R^B$; or $-C(R^B)_3$; wherein each occurrence of $R^B$ is independently hydrogen: halogen; a protecting group; aliphatic; heteroaliphatic; acyl; aryl moiety; heteroaryl ; hydroxyl: alkoxy; aryloxy; alkylthioxy; arylthioxy; amino; alkylamino; dialkylamino; beteroaryloxy; or heteroarylthioxy; each occurrence of R ''' is independently hydrogen; halogen; cyclic or acyclic , substituted or unsubstituted, branched or unbranched aliphatic; cyclic or acyclic, substituted or unsubstituted. branched or unbranched heteroaliphatic; substituted or unsubstituted , branched or unbranched acyl; substituted or unsubstituted, branched or unbranched aryl; substituted or unsubstituted, branched or unbranched heteroaryl; $OR^B$; $-C(=O)R^B$; $-CO_2R^B$; $-C(=O)N(R^B)_2$; $-CN$; $-SCN$; $-SR^B$; $-SOR^B$; $-SO_2R^B$; $-NO_2$; $-N(R^B)_2$; $-NHC(O)R^B$; or $-C(R^B)_3$; wherein each occurrence of $R^B$ is independently hydrogen; halogen; a protecting group; aliphatic; heteroaliphatic: acyl; aryl; heteroaryl; hydroxyl; alkoxy; aryloxy; alkylthioxy; arylthioxy; amino; alkylamino; dialkylamino; heteroaryloxy; or heteroarylthioxy; and n is an integer 1-4, inclusive, and pharmaceutically acceptable salts thereof.

In some embodiments, Z is $CH_2$, O, NH, S, C(R''')(R'''). In some embodiments, each occurrence of R' is independently hydrogen; hydroxyl, $OR^B$; wherein $R^B$ is hydrogen; a protecting group; $C_{1-6}$ alkyl; aryl; or heteroaryl. In some embodiments, each occurrence of R'' is independently hydrogen; hydroxyl, or ORB; wherein $R^B$ is hydrogen; a protecting group; or $C_{1-6}$ alkyl. In some embodiments, each occurrence of R''' is independently hydrogen; $C_{1-6}$ alkyl hydroxyl, or $OR^B$; wherein $R^B$ is hydrogen; a protecting group; or $C_{1-6}$ alkyl. In some embodiments, n is an integer 1-4, inclusive.

In certain embodiments, t he compound is of formula (IIa) wherein Z is $CH_2$, O, NH, S, or C(R''')(R'''); X is $CH_2$ or C(=O); Y is $CH_2$, or C(=O): each occurrence of R' is independently hydrogen; halogen ; cyclic or acyclic, substituted or unsubstituted, branched or unbranched aliphatic; cyclic or acyclic, substituted or unsubstituted, branched or unbranched heteroaliphatic; substituted car unsubs itaited,branched or unbranched a cy l substituted or unsubstituted, branched or unbranched aryl; substituted or unsubstituted, branched or unbranched heteroaryl; $OR^B$; —C(=O)$R^B$; —CO$_2R^B$; —C(=O)N($R^B$)$_2$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group: aliphatic; heteroaliphatic; acyl; aryl moiety; heteroaryl; hydroxyl; alkoxy, aryloxy; alkylthioxy; arylthioxy; amino ; alkylamino; dialkylamino; heteroaryloxy; or heteroarylthioxy; two R' can be taken together to form a fused cyclic group; each occurrence of R" is independently hydrogen, halogen; cyclic or acyclic, substituted or unsubstituted branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $OR^B$; —C(=O)$R^B$; —CO$_2R^B$; —C(=O)N($R^B$)$_2$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R_B$ is independently hydrogen: halogen; a protecting group: aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; or heteroarylthioxy; each occurrence of R'" is independently hydrogen; halogen; cyclic or acyclic, substituted or unsubstituted, branched or unbranched aliphatic; cyclic or acyclic, substituted or unsubstituted , branched or unbranched heteroaliphatic; substituted or unsubstituted, branched or unbranched acyl; substituted or unsubstituted, branched or unbranched aryl; substituted or unsubstituted, branched or unbranched heteroaryl; $OR^B$; —C(=O)$R^B$; —CO$_2R^B$; —C(=O)N($R^B$)$_2$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting, group; aliphatic; heteroaliphatic; acyl; aryl; heteroaryl; hydroxyl; alkoxy; aryloxy; alkylthioxy; arylthioxy ; amino; alkylamino; dialkylamino ; heteroaryloxy; or heteroalythioxy; and n is an integer 1-4, inclusive, and pharmaceutically acceptable salts thereof.

In some embodiments, Z is CH$_2$, O, NH, S, C(R'")(R'"). In some embodiments, X is CH$_2$, or C(=O). In some embodiments, Y is CH$_2$, or C(=O). In some embodiments, each occurrence of R' is independently hydrogen; hydroxyl, $OR^B$; wherein $R^B$ is hydrogen; a protecting group; C$_{1-6}$ alkyl; aryl; or heteroaryl. In some embodiments, each occurrence of R" is independently hydrogen; hydroxyl, or $OR^B$; wherein $R^B$ is hydrogen; a protecting group; or C$_{1-6}$alkyl. In some embodiments each occurrence of R'" is independently hydrogen; C$_{1-6}$alkyl hydroxyl, or $OR^B$; wherein $R^B$ is hydrogen; a protecting group; or C$_{1-6}$alkyl. In some embodiments n is an integer 1-4, inclusive.

In certain embodiments, the compound is a formula (IIIa) wherein each occurrence of R' is independently hydrogen; halogen; cyclic or acyclic, substituted or unsubstituted, branched or unbranched aliphatic; cyclic or acyclic: substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $OR^B$; —C(=O)$R^B$; —CO$_2R^B$; —C(=O)N($R^B$)$_2$; —CN; —SCN; —S$R^B$; —SO$R^B$; —SO$_2R^B$; —NO$_2$; —N($R^B$)$_2$; —NHC(O)$R^B$; or —C($R^B$)$_3$ wherein each occurrence of $R_B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylainino; heteroaryloxy; or heteroarylthioxyl, and pharmaceutically acceptable salts thereof.

In some embodiments each occurrence of R' is independently hydrogen; hydroxyl, $OR^B$; wherein $R^B$ is hydrogen; a protecting group; C$_{1-6}$ alkyl; aryl; or heteroaryl.

In certain embodiment, the compound is of formula (IVa) or (IVb) wherein X is CH$_2$, or C(=O); Y is CH$_2$, or C(=O); each occurrence of R'" each occurrence of R" is independently hydrogen; C$_{1-6}$alkyl hydroxyl, or $OR^B$; wherein $R^B$ is hydrogen; a protecting group; or C$_{1-6}$alkyl; and pharmaceutically acceptable salts thereof.

Figure 12C:
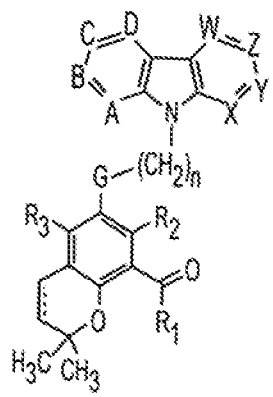
Figure 12D:
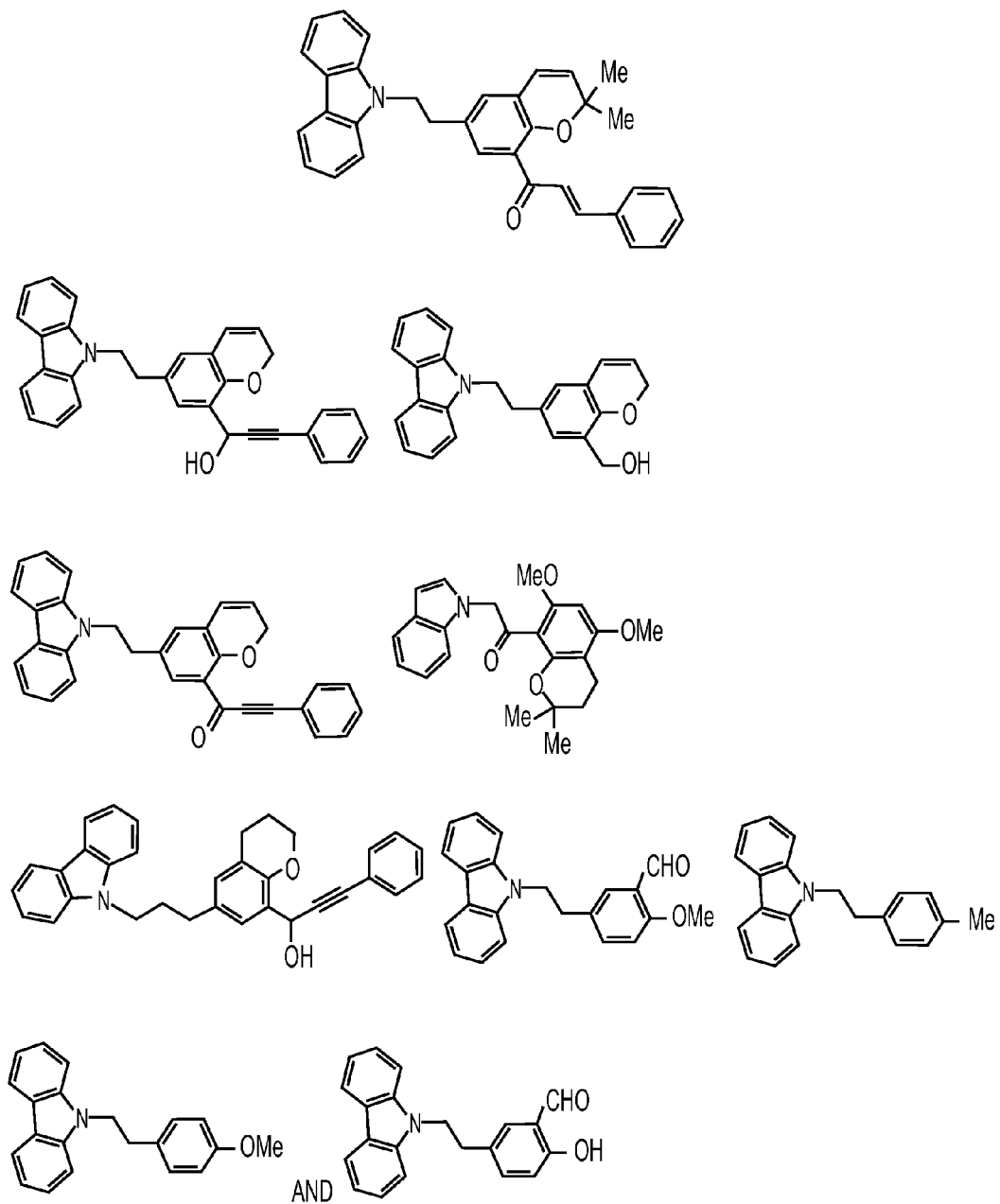

In certain embodiments the compound is of formula (V) are as disclosed in FIGS. 12C and 12D. In some embodiments, the compound of formula (Ia), (IIa), (IIIa), (IVa), or (V) as disclosed herein does not include any of N-phenethyl-carbazolen (SMILES: C(Cn1c2ccccc2c2ccccc12)c1ccccc1), crotmadine (SMILES: CC1(C)CCc2c(O)ccc(C(.dbd.O)\C=C\c3ccc(O)cc3)c201), 9-(1H-inden-2-yl)-9H-carbazole (SMILES: C1C(=Cc2ccccc12)n1c2ccccc2c2ccccc12), rottlerin (mallatoxin ), NDGA derivative tetra-a-methyl nordihydroguaiaric acid (M.sub.4N or terameprocol), UNC-01(7-0H staurosporine) and CGP41251 (PKC412, 4'-N-benzoyl staurosporin , KA1-9803.

Pharmaceutical Compositions

Aspects of the present invention relate to the use of any or, or a combination of compounds of formula (Ia), (IIa), (IIIa), (IVa), or (V) as described herein as an inhibitor of PKC delta, In particular, a compound of (Ia), (IIa), (IIIa), (IVa), or (V) as disclosed herein selectively inhibits PKC delta over other PKC isoforms. In particular a compound of formula ((Ia), (IIa), (IIIa), (IVa), or (V) as disclosed herein as a selective PKC delta inhibitors are advantageous over existing PKC delta inhibitors, as they are more potent at inhibiting cell proliferation and are non-toxic to cells with normal levels p21 Ras signaling.

Additionally, while some PKC delta inhibitors are used in combination, for example, rottlerin and straurosporine, the present PKC delta inhibitor compounds of formula (Ia), (IIa), (IIIa), (IVa), or (V) are advantageous at inhibiting PKC delta compounds in a single molecule.

The present invention provides novel compounds useful in the treatment of diseases or disorders associated with PKC delta activity. The compounds are useful in the treatment of a disease or condition that benefit from inhibition of PKC delta, for example, in a disease or condition where there is an elevation or increase in the activity and/or expression of PKC delta. In some embodiments, the compounds as disclosed herein are useful for methods for the treatment or prevention of disorders where inhibition of PKC delta is desirable, for example, diseases associated with impaired insulin sensitivity or fatty liver disease (FLD), including hepatic steatosis and type 2 diabetes, and non-alcoholic steatohepatitis (NASH), according to the methods as disclosed in International Application WO/2011/041385 which is incorporated herein in its entirety by reference.

In certain embodiments, the inventive compounds as disclosed herein are useful in the treatment of proliferative diseases, such as cancer. In some embodiments, the cancer is for example, a bronchopulmonary cancer, a gastrointestinal cancer or a pancreatic neuroendocrine cancer, a carcinoid and/or neuroendocrine cancer, malignant melanoma, pancreatic, gastrointestinal or lung cancer. In some embodiments, a neuroendocrine cancer can be derived from a bronchopulmonary, or foregut or hindgut tumor. (e.g., neuroendocrine tumor of pulmonary and gastrointestinal origin).

In certain embodiments, the inventive compounds as disclosed herein are useful in the treatment of diseases characterized by proliferation of connective tissue cells, or excessive deposition of matrix by those cells, such as in the fibrotic diseases. The fibrotic diseases encompass a wide spectrum of clinical entities, including multisystemic diseases, such as systemic sclerosis (scleroderma), multifocal fibrosclerosis, sclerodermatous graft-versus-host disease in bone marrow transplant recipients, and nephrogenic systemic fibrosis, as well as organ-specific disorders, such as pulmonary, liver, and kidney fibrosis. Specifically included in these fibrotic diseases are: Chronic Kidney Disease, Liver Fibrosis, Pulmonary/Lung Fibrosis, Systemic Sclerosis, Idiopathic pulmonary fibrosis; Cystic fibrosis, Cirrhosis, Endomyocardial fibrosis (heart); Mediastinal fibrosis (soft tissue of the mediastinum), Myelofibrosis (bone marrow), Retroperitoneal fibrosis (soft tissue of the retroperitoneum), Progressive massive fibrosis (lungs); a complication of coal workers' pneumoconiosis, Nephrogenic systemic fibrosis (skin), Crohn's Disease (intestine), Keloid (skin), Old myocardial infarction (heart), Scleroderma/systemic sclerosis (skin, lungs), Arthrofibrosis (knee, shoulder, other joints), and some forms of adhesive capsulitis (shoulder), and fibrosis following radiation ("post-radiation fibrosis"), and following administration of certain drugs, such as bleomycin ("bleomycin-induced pulmonary fibrosis").

Although their etiology and causative mechanisms differ, the fibrotic diseases share the common feature of disordered and exaggerated deposition of extracellular matrix in affected tissues. Elevated expression of genes encoding extracellular matrix proteins is a common and characteristic feature of these conditions, and the resulting fibrosis disrupts the normal architecture of the affected organs, which ultimately leads to their dysfunction and failure. The persistent activation of fibroblastic cells distinguishes controlled repair, such as that occurring during normal wound healing, from the uncontrolled fibrosis that is the hallmark of this group of diseases. Transforming growth factor-$\beta$ (TGF-$\beta$) is a critical mediator in the pathogenesis of tissue fibrosis. One TGF-$\beta$ pathway involves protein kinase C-delta (PKC-delta). In response to TGF-$\beta$, PKC delta is phosphorylated; phosphorylated PKC delta then removes inhibitory factors from the collagen gene promoter in the nucleus, which increases the transcriptional activity of the collagen gene. Inhibition of PKC-delta by pharmacologic or molecular biological techniques diminished the increased collagen gene expression induced by TGF-$\beta$ and that of cultured systemic sclerosis fibroblasts (Jimenez S A, Gaidarova S, Saitta B, Sandorfi N, Herrich D J, Rosenbloom J C. et al., Role of protein kinase C-delta in the regulation of collagen gene expression in scleroderma fibroblasts. J Clin Invest. 2001; 1081395-403).

Accordingly, in another aspect of the present invention, pharmaceutical compositions are provided, which comprise any one of the compounds described herein (or a prodrug, pharmaceutically acceptable salt or other pharmaceutically acceptable derivative thereof) and optionally a pharmaceutically acceptable excipient. In certain embodiments, these compositions optionally further comprise one or more additional therapeutic agents. Alternatively, a compound of this invention may be administered to a patient in need thereof in combination with the administration of one or more other therapeutic agents. For example, in the treatment of cancer, an additional therapeutic agent for conjoint administration or inclusion in a pharmaceutical composition with a compound of this invention may be an approved chemotherapeutic agent.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As described above, the pharmaceutical compositions of the present invention optionally comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, antioxidants, solid binders, lubricants, and the like, as suited to the particular dosage form desired. *Remington's Pharmaceutical Sciences*, Sixteenth Edition, E. W. Martin (Mack Publishing Co., Easton, Pa., 1980) discloses various excipients used in formulating pharmaceutical compositions and known techniques for the preparation thereof. Except insofar as any conventional excipient medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyllaurate; agar, buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives, and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable media prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monosteamte, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols, and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a excipient system. Pharmaceutically effective excipients include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other excipient known in the art for topically administering pharmaceuticals. A more complete listing of art-known carvers is provided by reference texts that are standard in the art, for example, *Remington's Pharmaceutical Sciences*, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyarrisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H.I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyllaurate, glycerol monooleate, and propylene glycol monooleate), and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable excipient and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix (e.g., PLGA) or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another immunomodulatory agent or anti-cancer agent), or they may achieve different effects (e.g., control of any adverse effects).

For example, other therapies or anticancer agents that may be used in combination with the inventive compounds of the present invention for cancer therapy include surgery, radiotherapy (in but a few examples, y-radiation, neutron beam radiotherapy, electron beam radiotherapy, proton therapy, brachytherapy, and systemic radioactive isotopes, to name a few), endocrine therapy, biologic response modifiers (interferon, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ion (Cisplatin, Carboplatin), enzymes (Asparaginase), and hormones (Tamoxifen, Leuprelide, Flutamide, and Megestrol), to name a few. For a more comprehensive discussion of updated cancer therapies see, *The Merck Manual*, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (at world-wide web at "fda.gov/cder/cancer/draglis&ame").

In certain embodiments, the pharmaceutical compositions of the present invention further comprise one or more additional therapeutically active ingredients (e.g., chemotherapeutic and/or palliative). For purposes of the invention, the term "palliative" refer, to treatment that is focused on the relief of symptoms of a disease and/or side effects of a therapeutic regimen, but is not curative. For example, palliative treatment encompasses painkillers, anti-nausea medication and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

Additionally, the present invention provides pharmaceutically acceptable derivatives of the inventive compounds, and methods of treating a subject using these compounds, pharmaceutical compositions thereof, or either of these in combination with one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

Another aspect of the invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the topical delivery of the inventive compounds. Optionally associated with such container(s) can be a notice in the form prescribed by a governmental agency regulating the manufacture, use or sale of pharmaceutical products, which notice reflects approval by the agency of manufacture, use or sale for human administration.

Pharmaceutical Uses and Methods of Treatment

One aspect of the present invention relates to the use of the compounds of formula (Ia), (IIa), (IIIa), (IVa ), or (V) as disclosed herein in a method to treat a disease or disorder associated with aberrant PKC delta activity. Accordingly, in some embodiments, the compounds are useful in the treatment of a disease or condition that benefit from inhibition of PKC delta, fur example, in a disease or condition where there is an elevation or increase in the activity and/or expression of PKC delta, In general , methods of using the compounds of the present invention comprise administering to a subject in need thereof a therapeutically effective amount of a compound of the present invention. The compounds of the invention are generally inhibitors of PKC delta activity. As discussed above, the compounds of the invention are typically inhibitors of PKC delta and, as such, are useful in the treatment of disorders where PKC delta is increased or overexpressed. Diseases associated with PKC delta may be treated by an inventive compound that inhibits PKC delta.

PKC Delta

Without wishing to be hound by theory, there are at least 12 PKC iso forms that are classified into three subfamilies according to the structure of the N-terminal regulatory domain, which determines their sensitivity to the second messengers $Ca_2$ and diacylglycerol (DAG). Despite the high degree of homology, however, there is a surprising degree of non-redundancy. Thus, individual PKC isoforms mediate different and unique cellular functions in different cell types and different tissues. PKC delta belongs to the subfamily of novel isoforms (PKC δ, PKCεPKCθ and PKCη), which are insensitive to $Ca_2$ PKC delta is widely regarded as having pro-apoptotic properties. Caspase activation mediates cleavage of PKC delta which results in release of the active catalytic domain. In addition, PKC delta activity is known to initiate a number of pro-apoptotic signals, such as increased expression and stability of p53(Johnson C L, 2002 and Abbas T, 2004), mitochondria cytochrome C release Majumder P K, 2000and Basu A, 2001 and c-Abl activation. Under certain conditions however. PKC delta has been reported to have a protective role in cell survival. PKC delta has also been reported to regulate B-lymphocyte survival. PKC delta also mediates tissue fibrosis in part by stimulation the synthesis of collagen and other components of the extracellular matrix. Knock-out experiments have shown that PKC delta deficient mice have a deregulated immune system and develop autoimmue disease. but are fertile and grow to adulthood.

Aspects of the present invention relate to the use of any or, or a combination of compounds of formula (Ia), (IIa), (IIIa), (IVa), or (V) as disclosed herein as an inhibitor of PKC delta. In particular, a compound of (Ia), (IIa), (IIIa), (IVa) or (V) as disclosed herein selectively inhibits PKC delta over other PKC isoforms. In particular, a compound of formula (Ia), (IIa), (IIIa), (IVa), or (V) as disclosed herein as a selective PKC delta inhibitors are advantageous over existing PKC delta inhibitors. as they are more potent at inhibiting cell proliferation and are non-toxic to cells with normal levels p21 Ras signaling.

Accordingly, one aspect of the present invention relates to a method for treating a subject with a proliferative disorder, herein referred to as a cancer. In some embodiments, the method comprises determining the Ras genotype of the tumor, that is, looking for the presence of increased Ras signaling. A subject having, a tumor associated with increased Ras signaling in the tumor can he treated according to the methods as disclosed herein, and can be administered a PKC delta inhibitor compound of formula (Ia), (IIa), (IIIa), (IVa), or (V) as disclosed herein.

Other aspects of the present invention relate to methods for directing treatment of a subject with a tumor. The status o f the level of Ras signaling of the subject' s tumor indicates a subject amenable to treatment according to the methods and composition as disclosed herein. In some embodiments, a subject is amenable to treatment according to the methods and compositions using a compound of formula (Ia), (IIa), (IIIa), (IVa), or (V) as disclosed herein where the Ras signaling of the subject's tumor is increased relative to comparable cells.

One aspect of the present invention relates to a method for treating a subject with, or at risk for, developing, a tumor which has aberrantly increased Ras signaling, comprising obtaining a biological sample from the subject; determining whether the biological sample contains cells which have aberrantly increased Ras signaling; and administering, to the subject a composition comprising a PKC delta inhibitor of a compound of formula (Ia), (IIa), (IIIa), (IVa), or (V) as disclosed herein to the subject upon determination of the aberrantly increased Ras signaling, to thereby inhibit PKC delta in the cell. In one embodiment, the aberrantly increased Ras signaling results from one or more occurrences, including expression of activated Ras, over-expression of wild-type Ras, or over-activation of wild-type Ras.

Expression of activated Ras may be detected by ELISA, western blot, antibody staining, immunohistochemistry, immunofluorescence, or any combination thereof. Alternatively, it may be detected by determination of the presence of a mutation in a Ras nucleic acid sequence, by polymerase chain reaction, primer-extension, allele-specific probe hybridization, allele-specific primer extension, allele-specific amplification, nucleotide sequencing, 5' nuclease digestion, molecular beacon assay, oligonucleotide ligation assay, single-stranded conformation polymorphism, or combinations thereof.

Accordingly, in certain embodiments, the inventive compounds of formula (Ia), (IIa), (IIIa), (IVa), or (V) as disclosed herein are useful in a method for t he treatment of a proliferative disease or disorder. such as cancer or tumor. In some embodiments, the cancer is for example, a bronchopulmonary cancer, a gastrointestinal cancer or a pancreatic neuroendocrine cancer, a carcinoid and/or neuroendocrine cancer. a malignant melanoma, pancreatic. gastrointestinal or lung cancer. In some embodiments, a neuroendocrine cancer can be derived from a bronchopulmonary, or foregut or hindgut tumor (e.g., neuroendocrine tumor cell line of pulmonary and gastrointestinal origin).

In certain embodiments, the method involves the administration of a therapeutically effective amount of the compound or a pharmaceutically acceptable derivative thereof to a subject (including, but not limited to a human or animal) in need of treatment. In some embodiments, the subject in need of treatment has cancer, or is likely to get cancer.

In certain embodiments, the inventive compounds as useful for the treatment of cancer, including, but not limited to, bronchopulmonary cancer, a gastrointestinal cancer or a pancreatic neuroendocrine cancer, or a carcinoid and/or neuroendocrine cancer, a malignant melanoma, pancreatic, gastrointestinal or lung cancer. In some embodiments, a neuroendocrine cancer can be derived from a bronchopulmonary, or foregut or hindgut tumor.

In some embodiments, the methods as disclosed herein comprise administering to a subject with cancer a composition comprising a compound of formula (Ia), (IIa), (IIIa), (IVa), or (V) as disclosed herein, wherein a subject has a cancer selected from any or a combination of: glioblastoma, retinoblastoma, breast cancer. cervical cancer, colon and rectal cancer, leukemia, lymphoma, lung cancer (including, but not limited to small cell lung cancer), melanoma and/or skin cancer, multiple myeloma, non- Hodgkin 's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer). In some embodiments the cancer is not melanoma.

In some embodiments, the methods as disclosed herein comprise administering to a subject with cancer a composition comprising a compound of formula (Ia),(IIa), (IIIa), (IVa), or (V) as disclosed herein, wherein a subject has a cancer selected from any or a combination of , but not limited to breast cancer, cervical cancer, colon and rectal cancer, leukemia, lung cancer, melanoma, multiple myeloma, non -Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemia (e.g., myeloid, lymphocytic, myelocytic and lymphoblastic leukemias) and malignant melanomas. In still other embodiments, the inventive anticancer agents are active against solid tumors.

In some embodiments, compounds of the invention are useful in the treatment of proliferative diseases e.g., cancer, benign neoplasms, inflammatory disease, autoimmune diseases. In other embodiments, the inventive compounds are useful in the treatment of autoimmune diseases; allergic and inflammatory diseases; diseases of the central nervous system (CNS), such as neurodegenerative diseases (e.g. Huntington's disease); vascular diseases, such as restenosis; musculoskeletal diseases; cardiovascular diseases, such as stroke; pulmonary diseases; gastric diseases; infectious diseases, and fibrotic diseases, such as Chronic Kidney Disease, Liver Fibrosis, Pulmonary/Lung Fibrosis, Systemic Sclerosis, Idiopathic pulmonary fibrosis; Cystic fibrosis, Cirrhosis, Endomyocardial fibrosis (heart); Mediastinal fibrosis (soft tissue of the mediastinum), Myelofibrosis (bone marrow), Retroperitoneal fibrosis (soft tissue of the retroperitoneum), Progressive massive fibrosis (lungs); a complication of coal workers' pneumoconiosis, Nephrogenic systemic fibrosis (skin), Crohn's Disease (intestine), Keloid (skin), Old myocardial infarction (heart), Scleroderma/systemic sclerosis (skin, lungs), post-radiation fibrosis, and drug-induced fibrosis.

In another aspect of the invention, methods for the treatment of a cancer in a subject are provided, the method comprising administering a therapeutically effective amount of an inventive compound, as described herein, to a subject in need thereof. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result.

In some embodiments. U.S. Pat. Nos. 4,313,872 and 7,276,567 and International patent applications W02006/060196, W02005/065666, W020071106424 disclose use of PKC delta inhibitors for treatment of cancer. However, these applications do not teach, suggest or discuss usin g a compound o f formula (Ia), (IIa), (IIIa), (IVa) as disclosed herein for the treatment of cancer.

In certain embodiments, the inventive compound is administered parenterally. In certain embodiments, the inventive compound is administered intravenously. In certain embodiments, the inventive compound is administered topically. In certain embodiments of the present invention, a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells," as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like.

In some embodiments, the compounds as disclosed herein are useful for methods for the treatment or prevention of disorders where inhibition of PKC delta is desirable, for example, diseases associated with impaired insulin sensitivity or fatty liver disease (FLD), including hepatic steatosis and type 2 diabetes, and non-alcoholic steatohepatitis (NASH), according to the methods as disclosed in International Application W0/2011/041385 which is incorporated herein in its entirety by reference.

As disclosed here in the inventors have demonstrated the compounds of formula (Ia), (IIa), (IIIa), (IVa) or (V) as disclosed herein inhibit cell proliferation, in some embodiments the inventive compounds as disclosed herein can be used in a method to prevent restenosis of blood vessels in a subject with a trauma such as angioplasty and ste nting. For example. encompassed herein in the invention, the compounds of formula (Ia), (IIa), (IIIa), (IVa), or (V) are useful as a coating for implanted medical devices, such as tubings , shunts , catheters. artificial implants, pins. electrical implants such as pacemakers, and especially for arterial or venous stents, including balloon-expandable stents. In certain embodiments inventive compounds are encompassed for use in coating an implantable medical device, or alternatively, be passively adsorbed to the surface of the implantable device. In certain other embodiments, the inventive compounds may be formulated to be contained within, or, adapted to release by a surgical or medical device or implant, such as, for example, stents, sutures, indwelling catheters, prosthesis, and the like. For example, drugs having antiproliferative and anti-inflammatory activities have been evaluated as stent coatings. and have shown promise in preventing retenosis (See, for example. Presbitero et al., "Drug eluting stents do they make the difference?", Minerva Cardioangiol. , 2002,50(5):431-442; Ruygrok et al., "Rapamycin in cardiovascular medicine", Intern. Med. 2003,33(3)103-109: and Marx et al., "Bench to bedside: the development of rapa mycin and its application to sten t restenosis ", Circulation, 2001, 104(8): 852-855, each of these references is incorporated herein by reference in its entirety).

Accordingly, without wishing to be bound to theory, the compounds of formula (Ia), (IIa), (IIIa), (IVa), or (V) which inhibit cell proliferation and have antiproliferative effects can be used as stent coatings and/or in steal drug delivery devices. inter alia for the prevention of restenosis or reduction of restenosis rate in a subject, Suitable coatings and the general preparation of coated implantable devices are described in U.S. Pat. Nos. 6,099,562; 5,886,026; and 5,304,121 ; each of which is incorporated herein by reference. A variety of compositions and methods related to stem coating and/or local stem drug delivery for preventing restenosis are known in the art (see, for example. U.S. Pat. Nos. 6,517,889; 6,273,913 ; 6,258,121; 6,251,136; 6,248,127; 6,231,600; 6,203,551; 6,153,252; 6,071 ,305; 5,891,507; 5,837,313 and published U.S. patent application No.: US200110027340, each of which is incorporated herein by reference in its entirety).

In some embodiments, the compounds as disclosed herein can be used in a method to eliminate a biliary, gastrointestinal, esophageal, tracheal/bronchial, urethral, and/or vascular obstruction using a stent coated with a composition as disclosed herein. Methods for eliminating biliary, gastrointestinal, esophageal, tracheal/bronchial, urethral and/or vascular obstructions using stents are known in the art. The skilled practitioner will know how to adapt these methods in practicing the present invention. For example, guidance can be found in US. Patent Application Publication No.: 2003/0004209 in paragraphs [0146]-[0155], which paragraphs are hereby incorporated herein by reference.

Additionally, the present invention provides pharmaceutically acceptable derivatives of the inventive compounds, and methods of treating a subject using such compounds, pharmaceutical compositions thereof, or either of these in combination with one or more additional therapeutic agents.

Another aspect of the invention relates to a method of treating or lessening the severity of a disease or condition associated with a proliferation disorder in a patient. said method comprising a step of ad ministering to said patient. a compound of formula (Ia), (IIa), (IIIa), (IVa) or (V) or a composition comprising said compound.

The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, mute of administration, and rate of excretion of the specific compound employed; the duration of the treatment; drugs used in combination or coincidental with the specific compound employed; and like factors well known in the medical arts (see, for example, *Goodman and Gilman's The Pharmacological Basis of Therapeutics*, Tenth Edition, A. Gilman, J. Hardman and L. Limbird, eds., McGraw-Bill Press, 155-173, 2001, which is incorporated herein by reference in its entirety).

Another aspect of the invention relates to a method for inhibiting PKC delta activity in a biological sample or a patient, which method comprises administering to the patient, or contacting said biological sample with an inventive compound or a composition comprising said compound.

In some embodiments, a subject is selected to he administered a composition comprising a compound of formula (Ia), (IIa), (IIIa) (IVa), or (V) where the subject is selected if they have an elevated or increased level of Ras signaling in a biological sample obtained from the subject, where the biological sample is a cancer sample, or biopsy sample obtained from the subject. In some embodiments, an increased level of ms signaling is a statistically significant increase level of Ras signaling, as compared to a normal sample (e.g., a nominal tissues sample 1mm a normal subject and/or a non-malignant or non-cancerous tissue sample). Ras signaling can be measured by any means commonly known in the art, tor example, by any means as disclosed in International Application WO/20071106424, which is incorporated herein in its entirety by reference.

Activated Ras, is typically detected directly (i.e., the antibody to the antigen of interest is labeled) or indirectly (i.e., a secondary antibody that recognizes the antibody to the antigen of interest is labeled) using a detectable label. The particular label or detectable group used in the assay is usually not critical, as long as it does not significantly interfere with the specific binding of the antibodies used in the assay. The amount of activated Ras protein in a sample can be measured indirectly by measuring the amount of added (exogenous) activated Ras protein displaced from a capture agent, i.e. an anti-activated Ras antibody, by the activated Ras in the sample. In noncompetitive assays, the amount of activated Ras in a sample is directly measured. In some embodiments, a noncompetitive "sandwich" assay can be used to measure activated Ras where the capture agent (e.g., a first antibody) is bound directly to a solid support (e.g., membrane, microtiter plate, test tube, dipstick, glass or plastic bead) where it is immobilized. The immobilized agent then captures any antigen of interest present in the sample. The immobilized antigen of interest can then be detected using a second labeled antibody to the antigen of interest. Alternatively, the second antibody can be detected using a labeled secondary antibody that recognizes the second antibody.

In some embodiments, a method measuring the expression of activated Ras, is by antibody staining with an antibody that binds specifically to the antigen employing a labeling strategy that makes use of luminescence or fluorescence. Such staining may be carried out on fixed tissue or cells that are ultimately viewed and analyzed under a microscope. Staining carried out in this manner can be scored visually or by using optical density measurements. Staining may also be carried out using either live or fixed whole cells in solution, e.g. cells isolated from blood or tumor biopsy. Such cells can be analyzed using a fluorescence activated cell sorter (FACS), which can determine both the number of cells stained and the intensity of the luminescence or fluorescence. Such techniques are well known in the art, and exemplary techniques are described in Luwor et al. ((2001), Cancer Res. 61:5355-61). One of skill in the art will realize that other techniques of detecting expression might be more or less sensitive than these techniques. As meant herein, cells express little or no antigen if little or no antigen can be detected using an antibody staining technique that relies on luminescence or fluorescence.

Alternatively, expression of activated Ras in cells, particularly tumor cells, can be detected in vivo in a subject by introducing into the subject a labeled antibody to activated Ras protein. For example, the antibody can be labeled with a radioactive marker whose presence and location in a subject can be detected by standard imaging techniques.

In some embodiments, immunohistochemistry ("IHC") and immunocytochemistry ("ICC") techniques, for example, may be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of a specific antibody, wherein antibodies are used to specifically target molecules inside or on the surface of cells. The antibody typically contains a marker that will undergo a biochemical reaction, and thereby experience a change color, upon encountering the targeted molecules. In some instances, signal amplification may be integrated into the particular protocol, wherein a secondary antibody, that includes the marker stain, follows the application of a primary specific antibody. Immunohistochemical assays are known to those of skill in the art (e.g., see Jalkanen, et al., J. Cell. Biol. 101:976-985 (1985); Jalkanen, et al., J. Cell. Biol. 105:3087-3096 (1987).

In some embodiments, for immunohistochemistry, tissue sections are obtained from a patient and fixed by a suitable fixing agent such as alcohol, acetone, and paraformaldehyde, to which is reacted an antibody. Conventional methods for immunohistochemistry are described in Harlow and Lane (eds) (1988) In "Antibodies A Laboratory Manual", Cold Spring Harbor Press, Cold Spring Harbor, N.Y.; Ausbel et al (eds) (1987), in Current Protocols In Molecular Biology, John Wiley and Sons (New York, N.Y.). Biological samples appropriate for such detection assays include, but are not limited to, cells, tissue biopsy, whole blood, plasma, serum, sputum, cerebrospinal fluid, breast aspirates, pleural fluid, urine and the like. For direct labeling techniques, a labeled antibody is utilized. For indirect labeling techniques, the sample is further reacted with a labeled substance.

Alternatively, immunocytochemistry may be utilized. In general, cells are obtained from a patient and fixed by a suitable fixing agent such as alcohol, acetone, and paraformaldehyde, to which is reacted an antibody. Methods of immunocytological staining of human samples is known to those of skill in the art and described, for example, in Brauer et al., 2001 (FASEB J, 15, 2689-2701), Smith-Swintosky et al., 1997. Immunological methods of the present invention are advantageous because they require only small quantities of biological material, e.g., a biopsy cancer tissue sample. Such methods may be done at the cellular level and thereby necessitate a minimum of one cell. Preferably, several cells are obtained from a patient affected with or at risk for developing cancer and assayed according to the methods of the present invention.

In some embodiments, activated Ras can be detected by a mutation detection kit and/or systems, including but not limited to, packaged probe and primer sets (e.g., TaqMan probe/primer sets), arrays/microarrays of nucleic acid molecules, and beads that contain one or more probes, primers, or other detection reagents for detecting activated Ras mutations. The kits/systems can optionally include various electronic hardware components; for example, arrays ("DNA chips") and microfluidic systems ("lab-on-a-chip" systems, biomedical micro-electro-mechanical systems (bioMEMs), or multi-component integrated systems) provided by various manufacturers typically comprise hardware components. Other kits/systems (e.g., probe/primer sets) may not include electronic hardware components, but may be comprised of, for example, one or more mutation detection reagents (along with, optionally, other biochemical reagents) packaged in one or more containers.

In some embodiments, the subject administered a composition comprising a compound of formula (Ia), (IIa),(IIIa), (IVa) or (V) has aberrantly increased Ras signaling, e.g., as a result of expression of activated Ras. In some embodiments, aberrantly increased Ras signaling is determined by detection of an activated Ras protein or a nucleotide sequence encoding an activated form of Ras protein. In some embodiments, increased Ras signaling is associated with activation of a pathway selected from the group consisting of Rafl/MAPK, RasGDS/Ras/Rho, P13K, and combinations thereof. In some embodiments, activated form of Ras is selected from the group consisting of K-ras, H-ras, and N-ras. In some embodiments, aberrantly increased Ras signaling results from overexpression of wild-type Ras, or from increased activation of one or more effector pathways downstream of Ras.

Furthermore, after formulation with an appropriate pharmaceutically acceptable excipient in a desired dosage, the pharmaceutical compositions of this invention can be administered to humans and other animals orally, rectally, parenterally, intracisternally, intravaginally, intraperitoneally, topically (as by powders, ointments, creams or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Uses

The present invention provides novel compounds useful in the treatment of diseases or disorders associated with PKC delta activity. The compounds are useful in the treatment of diseases or condition that benefit from inhibition of PKC delta. In certain embodiments, the inventive compounds as useful for the treatment of cancer, including, but not limited to, bronchopulmonary cancer, a gastrointestinal cancer or a pancreatic neuroendocrine cancer, or a carcinoid and/or neuroendocrine cancer, a malignant melanoma, pancreatic, gastrointestinal or lung cancer. In some embodiments, a neuroendocrine cancer can be derived from a bronchopulmonary, or foregut or hindgut tumor.

In certain embodiments, the inventive compounds are useful in the treatment of cellular proliferative diseases, such as cancer (e.g., cutaneous T-cell lymphoma) or benign proliferative diseases such as fibrotic diseases including systemic sclerosis, radiation-induced fibrosis and pulmonary fibrosis; autoimmune diseases; allergic and inflammatory diseases; diseases of the central nervous system (CNS), such as neurodegenerative diseases (e.g. Huntington's disease); vascular diseases, such as restenosis; musculoskeletal diseases; cardiovascular diseases; stroke; pulmonary diseases; gastric diseases; and infectious diseases.

In certain embodiments, the compounds of the present invention are useful as inhibitors of PKC delta and thus are useful as antiproliferative agents, and thus may be useful in the treatment of cancer, by effecting tumor cell death or inhibiting the growth of tumor cells, and in other diseases characterized by excessive proliferation of cells, such as fibrotic diseases, by inhibiting the proliferation of cells contributing to fibrosis or collagen production by these cells. In certain exemplary embodiments, the inventive compounds are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In certain embodiments, the inventive compounds are active against cutaneous T-cell lymphoma. Additionally, as described herein, the inventive compounds may also be useful in the treatment of protozoal infections. Additionally, as described herein, the inventive compounds may also be useful in the treatment of autoimmune or inflammatory diseases and fibrotic diseases. Furthermore, as described herein, the inventive compounds may also be useful in the treatment of neurodegenerative diseases. As described herein, the inventive compounds may also be useful in the treatment of cardiovascular diseases.

Activated Ras proteins play a key role in the development of many human cancers. "Ras" and "p21Ras" are used interchangeably herein. Mutations in Ras are observed in approximately one third of all tumors (Bos, Cancer Res 49:4682-4689 [1989]; and Clark and Der, in GTPases in Biology [eds. Dickey and Birmbauer], Springer-Verlag London Ltd., pp. 259-287 [1993]). Indeed, the frequency of Ras mutation approaches 100% in some types of tumors (e.g., pancreatic adenocarcinoma). These mutated Ras proteins demonstrate decreased inherent GTPase activity, and are resistant to the action of GTPase-activating proteins (GAPs). Thus, these mutations, e.g., mutations localized in codons 12, 13, 59, 61, 63, 116, 117, and 146, are activating mutations resulting in the Ras protein being locked in an active conformation, leading ultimately to inappropriate cell proliferation signaling. Furthermore, activated forms of the Ras protein are useful in the induction of tumors, thereby providing direct evidence for Ras involvement in malignant cell transformation and tumorigenesis. Moreover, deletion of the activated Ras gene from tumor cell lines impairs their tumorigenicity (Paterson et al., Cell 51:803-812 [1987]; and Shirasawa et al., Science 260: 85-88 [1993]). Three closely related Ras genes are H-ras (GenBank Accession No. NM_005343, K-ras (GenBank Accession No. NM_004985;) and N-ras (GenBank Accession No. NM_002524). Wild-type Ras proteins, found in normal, healthy individuals, cycle between an active (GTP bound) state and an inactive (GDP bound) state. Activated Ras proteins result from activating mutations which have decreased inherent GTPase activity, and are resistant to the action of GTPase-activating proteins (GAPs), the natural negative regulators of Ras proteins. Thus, these mutations, e.g., mutations localized in codons 12, 13, 59, 61, 63, 116, 117, and 146, are activating mutations resulting in the Ras protein being locked in an active conformation. The presence of the activated form of Ras in a cell leads ultimately to inappropriate cell proliferation signaling.

Activated Ras proteins play a key role in the development of many human cancers. Such mutations in Ras are observed in approximately one third of all tumors (Bos, Cancer Res 49:4682-4689 [1989]; and Clark and Der, in GTPases in Biology [eds. Dickey and Birmbauer], Springer-Verlag London Ltd., pp. 259-287 [1993]). Indeed, the frequency of Ras mutation approaches 100% in some types of tumors (e.g., pancreatic adenocarcinoma). In addition to the correlation between the presence of activated Ras mutations in a high percentage of a variety of cancers, a wealth of experimental evidence indicates that increased Ras activity is involved in malignant cell transformation and tumorigenesis. For example, activated forms of the Ras protein can be used to experimentally transform cells in culture and induce tumors in animal models. Furthermore, deletion of the activated Ras gene from tumor cell lines impairs their tumorigenicity (Paterson et al., Cell 51:803-812 [1987]; and Shirasawa et al., Science 260:85-88 [1993]).

In certain exemplary embodiments, the compounds of the invention are useful for treatment of diseases and disorders where there is aberrant or increased Ras signaling. Such disorders are disclosed in International Application WO2007/0106424, and US patent application US2009/0330503, both incorporated herein in their entirety by reference.

Aberrant signaling through Ras signaling pathways occurs as a result of several different classes of mutational damage in tumor cells. Table 1 provides a list of methods of increased activation of Ras signaling pathway in different tumors, and encompasses cancers amenable to be treated according to the methods and compositions as disclosed herein.

TABLE 1

Activation of RAS signaling pathways in different tumors

| Defect or Mutation | Tumor Type | Frequency |
|---|---|---|
| RAS mutation | Pancreas | 90 (K) |
| | Lung adenocarcinoma (non-small-cell) | 35 (K) |
| | Colorectal | 45 (K) |
| | Thyroid (follicle) | 55 (H, K, N) |
| | Thyroid (undifferentiated, papillary) | 60 (H, K, N) |
| | Seminoma | 45 (K, N) |
| | Melanoma | 34 (N) |
| | Bladder | 10 (H) |
| | Liver | 30 (N) |
| | Kidney | 10 (H) |
| | Myelodysplastic syndrome | 40 (N, K) |
| | Acute myelogenous leukemia | 30 (N) |
| BRAF mutation | Melanoma | 66 |
| | Colorectal | 12 |
| EGFR overexpression | Most carcinomas | >50 |
| ERBB2 amplification | Breast | 30 |
| PTEN loss | Glioblastoma multiforme | 20-30 |
| | Prostate | 20 |
| | Pancreas | 40 |
| AKT2 amplification | Ovarian | 12 |
| | Pancreas | 10 |
| PI3K amplification | Ovarian | 40 |

EGFR = epidermal growth factor receptor
PI3K = phosphotidylinositol-3-kinase
H, K and N refer to HRAS, KRAS and NRAS respectively
Table from: Downward J. Targeting RAS signalling pathways in cancer therapy. Nat Rev Cancer. 2003 Jan; 3(1): 11-22.

As detailed in the exemplification herein, in assays to determine the ability of compounds to inhibit PKC delta activity, certain inventive compounds may exhibit $IC_{50}$ values $\leq 100$ µM. In certain other embodiments, inventive compounds exhibit $IC_{50}$ values $\leq 50$ µM. In certain other embodiments, inventive compounds exhibit $IC_{50}$ values $\leq 40$ µM. In certain other embodiments, inventive compounds exhibit $IC_{50}$ values $\leq 30$ µM. In certain other embodiments, inventive compounds exhibit $IC_{50}$ values $\leq 20$ µM. In certain other embodiments, inventive compounds exhibit $IC_{50}$ values $\leq 10$ µM. In certain other embodiments, inventive compounds exhibit $IC_{50}$ values $\leq 7.5$ µM. In certain other) embodiments, inventive compounds exhibit $IC_{50}$ values $\leq 5$ µM. In certain other embodiments, inventive compounds exhibit $IC_{50}$ values $\leq 2.5$ µM. In certain other embodiments, inventive compounds exhibit $IC_{50}$ values $\leq 1$ µM. In certain other embodiments, inventive compounds exhibit $IC_{50}$ values $\leq 0.75$ µM. In certain embodiments, inventive compounds exhibit $IC_{50}$ values $\leq 0.5$ µM. In certain other embodiments, inventive compounds exhibit $IC_{50}$ values $\leq 0.25$ µM. In certain embodiments, inventive compounds exhibit $IC_{50}$ values $\leq 0.1$ M. In certain embodiments, inventive compounds exhibit $IC_{50}$ values $\leq 75$ nM. In certain embodiments, inventive compounds exhibit $IC_{50}$ values $\leq 50$ nM. In certain embodiments, inventive compounds exhibit $IC_{50}$ values $\leq 25$ nM. In certain embodiments, inventive compounds exhibit $IC_{50}$ values $\leq 10$ nM.

In assays to determine the ability of compounds to inhibit cancer cell growth certain inventive compounds may exhibit $IC_{50}$ values $\leq 100$ µM. In certain other embodiments, inventive compounds exhibit $IC_{50}$ values $\leq 50$ µM. In certain other embodiments, inventive compounds exhibit $IC_{50}$ values $\leq 40$ µM. In certain other embodiments, inventive compounds exhibit $IC_{50}$ values $\leq 30$ µM. In certain other embodiments, inventive compounds exhibit $IC_{50}$ values $\leq 20$ µM. In certain other embodiments, inventive compounds exhibit $IC_{50}$ values $\leq 10$ µM. In certain other embodiments, inventive compounds exhibit $IC_{50}$ values $\leq 7.5$ µM. In certain embodiments, inventive compounds exhibit $IC_{50}$ values $\leq 5$ µM. In certain other embodiments, inventive compounds exhibit $IC_{50}$ values $\leq 2.5$ µM. In certain embodiments, inventive compounds exhibit $IC_{50}$ values $\leq 1$ µM. In certain embodiments, inventive compounds exhibit $IC_{50}$ values $\leq 0.75$ µM. In certain embodiments, inventive compounds exhibit $IC_{50}$ values $\leq 0.5$ µM. In certain embodiments, inventive compounds exhibit $IC_{50}$ values $\leq 0.25$ µM. In certain embodiments, inventive compounds exhibit $IC_{50}$ values $\leq 0.1$ µM. In certain other embodiments, inventive compounds exhibit $IC_{50}$ values $\leq 75$ nM. In certain other embodiments, inventive compounds exhibit $IC_{50}$ values $\leq 50$ nM. In certain embodiments, inventive compounds exhibit $IC_{50}$ values $\leq 25$ nM. In certain embodiments, inventive compounds exhibit $IC_{50}$ values $\leq 10$ nM. In other embodiments, exemplary compounds exhibited $IC_{50}$ values $\leq 7.5$ nM. In other embodiments, exemplary compounds exhibited $IC_{50}$ values $\leq 5$ nM.

In connection with the administration of the drug, an "effective amount" indicates an amount that results in a beneficial effect for at least a statistically significant fraction of patients, such as an improvement of symptoms, a cure, a reduction in disease load, reduction in tumor mass or cell numbers, extension of life, improvement in quality of life, or other effect generally recognized as positive by medical doctors familiar with treating the particular type of disease or condition.

The effective dosage of active ingredient employed may vary depending on the particular compound employed, the mode of administration and the severity of the condition being treated. The skilled artisan is aware of the effective dose for each patient, which may vary with disease severity, individual genetic variation, or metabolic rate. However, in general, satisfactory results are obtained when the compounds of the invention are administered at a daily dosage of from about 0.5 to about 1000 mg/kg of body weight, optionally given in divided doses two to four times a day, or in sustained release form. The total daily dosage is projected to be from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier.

This dosage regimen may be adjusted to provide the optimal therapeutic response. For example, several divided doses may be administered daily or the dose may be proportionally reduced as indicated by the exigencies of the therapeutic situation. The route of administration may be intravenous (I.V.), intramuscular (I.M.), subcutaneous (S.C.), intradermal (ID.), intraperitoneal (I.P.), intrathecal (I.T.), intrapleural, intrauterine, rectal, vaginal, topical, intratumor and the like. The compounds of the invention can be administered parenterally by injection or by gradual infusion over time and can be delivered by peristaltic means. Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, example, or using suppositories. For oral administration, the compounds of the invention are formulated into conventional oral administration forms such as capsules, tablets and tonics. For topical administration, the pharmaceutical composition (inhibitor of kinase activity) is formulated into ointments, salves, gels, or creams, as is generally known in the art. The therapeutic compositions of this invention, e.g., PKC delta inhibitors, are conventionally administered intravenously, as by injection of a unit dose, for example.

The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluents; i.e., carrier, or vehicle. The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual. The therapeutic composition useful for practicing the methods of the present invention, e.g. PKCdelta inhibitors, are described herein. Any formulation or drug delivery system containing the active ingredients, which is suitable for the intended use, as are generally known to those of skill in the art, can be used. Suitable pharmaceutically acceptable carriers for oral, rectal, topical or parenteral (including inhaled, subcutaneous, intraperitoneal, intramuscular and intravenous) administration are known to those of skill in the art.

The following examples illustrate embodiments of the invention, but should not be viewed as limiting the scope of the invention.

EXAMPLES

Cell Lines: BON1, a human foregut (pancreatic) carcinoid tumor cell line (Parekh et al. 1994) was obtained from Kjell Oberg (Uppsala University, Sweden) through Dr. Evan Vosburgh. H727 cells, derived from a human bronchopulmonary carcinoid tumor (Schuller et al. 1987), were purchased from ATCC. The CNDT 2.5 cell line, initially described as a human midgut carcinoid tumor cell line (Van Buren et al. 2007), was provided by Dr. Lee Ellis, (M D Anderson Cancer Center). The provenance of this cell line is currently under review by the originator. BON1, H727, MCF10 and CNDT 2.5 cells were propagated in 10% FBS (Invitrogen); Dulbecco's Modification of Earle's Media/Hams F-12 50:50 media (Cellgro); 2 mM L-Glutamine (Invitrogen); 200 U Penicillin/ml; 200 ug Streptomycin/ml (Invitrogen); 10 ng/ml Nerve Growth Factor (Invitrogen); 1×MEM Non-Essential Amino Acids (Cellgro); 1×MEM Vitamin Solution (Cellgro); 1 mM Sodium Pyruvate; 0.015 M HEPES buffer (pH7.3) (American Bioanalytical).

Clonogenic Assays: 100,000 cells were seeded on 100 mm dishes with 10 ml media per dish (Li et al. 2004). On day 4, cells were treated with a PKC delta inhibitor, or vehicle control for either 6, 18, 24 or 48 hours. Cells were trypsinized; counted via Trypan Blue Exclusion Method in order to determine the number of live cells in the sample, and 500 live cells were seeded in triplicate onto 6 well plates. Cells were monitored for appropriate colony size andre-fed every three to four days. At Day 17, cells were stained with ethidium bromide (Guda et al. 2007) and counted using UVP LabWorks software.

PKC Kinase Activity Assays: Assays were carried out using recombinant PKC alpha or PKC gamma, (Invitrogen) and the Omnia® Kinase Assays (Invitrogen) with a "PKC kinase-specific" peptide substrate. Incorporation of a chelation-enhanced fluorophore (CHEF) results in an increase in fluorescence $\lambda ex360/\lambda em485$) upon phosphorylation. The kit was used according to the manufacturer's instructions.

Reagents: Rottlerin was purchased from (EMD Biosciences). The PKC delta inhibitor KAMI is a chimeric molecule combining the chromene portion of rottlerin with the carbazole portion of staurosporine.

Cell Proliferation Assays—Cell proliferation was assessed using an MTT [3-(4,5-dimethylthiazol-2-yl)-2,5-diphenyltetrazolium bromide] assay (Roche, Mannheim, Germany). The number of viable cells growing in a single well on a 96-well microtiter plate was estimated by adding 10 ul of MTT solution (5 mg/ml in phosphate-buffered saline [PBS]). After 4 h of incubation at 37° C., the stain is diluted with 100 ul of dimethyl sulfoxide. The optical densities are quantified at a test wavelength of 570 nm and a reference wavelength of 690 nm on a multiwell spectrophotometer. In some assays, MTS was used as substrate (Promega, Madison, Wis.), and the absorbance of the product was monitored at 490 nm.

Cytotoxicity Assay: LDH release was assessed by spectrophotometrically measuring the oxidation of NADH in both the cells and media. Cells were seeded in 24-well plates, and exposed to PKC delta inhibitors or vehicle. After different times of exposure, cytotoxicity was quantified by a standard measurement of LDH release with the use of the LDH assay kit (Roche Molecular Biochemicals) according to the manufacturer's protocol. Briefly, total culture medium was cleared by centrifugation. For assay of released LDH, supernatants were collected. To assess total LDH in cells, Triton X-100 was added to vehicle (control) wells to release intracellular LDH. LDH assay reagent was added to lysates or supernatants and incubated for up to 30 min at room temperature in dark, the reaction was stopped, and the absorbance was measured at 490 nm. The percentage of LDH release was then calculated as the LDH in the supernatants as a fraction of the total LDH.

Immunoblot Analyses: Levels of proteins were measured and quantitated in carcinoid cell lines, as we have previously reported (Xia et al. 2007). Harvested cells were disrupted in a buffer containing 20 mM Tris (pH 7.4), 0.5% NP-40, and 250 mM NaCl. Total protein (40 g) was separated on 10% SDS-polyacrylamide gels and transferred to nitrocellulose membranes or PVDF membranes. Membranes are blocked overnight and probed with affinity-purified antibodies against PKC alpha and delta (BD Transduction Lab), or betta-actin (Sigma). After washing, the blots were incubated with horseradish peroxidase-conjugated secondary antibodies and visualized using the Amersham enhanced chemiluminescence ECL system, and quantitated by digital densitometry. Antibodies against human ERK, phospho-ERK, AKT and phospho-Ser473-AKT were purchased from Cell Signaling (Danvers, Mass.). GTP-bound Ras was assayed by affinity purification using a Raf-1/RBD agarose conjugate (Upstate Biotechnology, Lake Placid, N.Y.), and detected with a pan-Ras antibody (Cell Signaling, Danvers, Mass.), following the manufacturer's instructions.

Down-Regulation of PKC Delta by siRNA and Lentiviral Vectors: siRNA knockdown of PKC delta and PKC alpha: siRNA duplexes for PKC delta (siRNAs) are obtained from Qiagen (Valencia, Ca). The siRNA sequences for targeting PKC delta are PKC delta-siRNA-1 (5'-GAUGAAGGAG-GCGCUCAGTT-3'; SEQ ID NO 1) and PKC delta siRNA-2 (5'-GGCUGAGUUCUGGCUGGA-CTT-3'; SEQ ID NO 2). The corresponding scrambled siRNAs were used as negative control. These siRNA sequences were also cloned into the pRNA6.1-Neo vector with a GFP tag according to the manufacturer's instructions (GenScript, Piscataway, N.J.). siRNA for PKC alpha (PKCPKC alpha-V6) are purchased from Upstate (Lake Placid, N.Y.). Transfection of siRNA (oligo) is performed using 50 nM PKC delta siRNA, or the same amount of scrambled siRNA and Lipofectamine 2000 (Invitrogen, Carlsbad, Calif.), according to the manufacturer's instructions. Transfection of plasmid-based siRNA vectors are carried out using the same method. PKC delta protein levels were determined by immunoblot analysis (see below). The lentiviral vectors were previously described (Xia et al. 2009).

Statistical Analysis. Experiments were carried out in triplicate for all experimental conditions. Data are shown as mean±SD. Where applicable, a two-tailed Student's t test was performed on the means of two sets of sample data and considered significant if p≤0.05.

Example 1

Figure 1B:
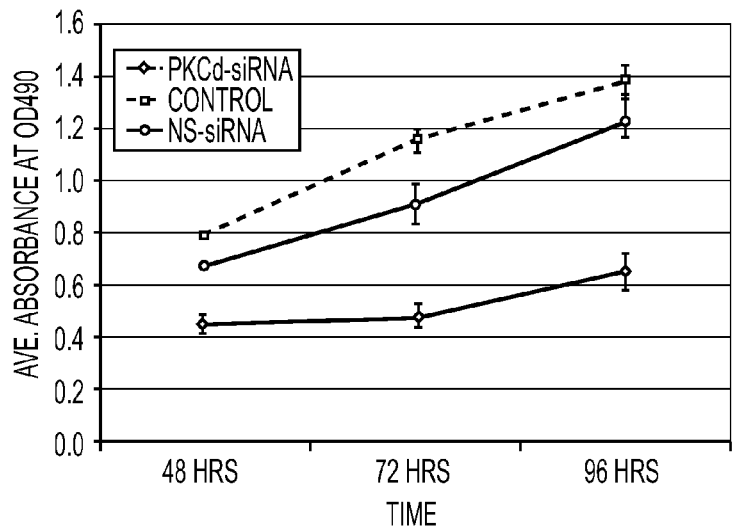
Figure 1C:
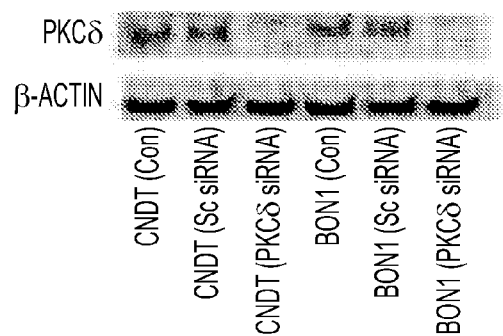

PKCd Depletion by siRNA Inhibits Proliferation and Induces Cytotoxicity in Human Neuroendocrine Cell Lines To determine the effects of specific PKC delta depletion on the proliferation and survival of human neuroendocrine tumor cell lines, we used PKC delta-specific siRNA to knockdown PKC delta mRNA/protein. Cell line studied for sensitivity included BONI, a human foregut (pancreatic) carcinoid tumor cell line; H727 cells, derived from a human bronchopulmonary carcinoid tumor; and the CNDT 2.5 cell line, a human cell line with neuroendocrine markers, initially described as a human midgut carcinoid tumor cell line. Exposure of the BONI and CNDT cell lines to PKC delta-specific siRNA in culture resulted in a profound inhibition of proliferation (FIG. 1). In contrast, exposure of the same cells to a control (scrambled siRNA) did not affect proliferation. Efficient knockdown of PKC delta protein by specific siRNA was verified by immunoblotting.

Figure 2A:
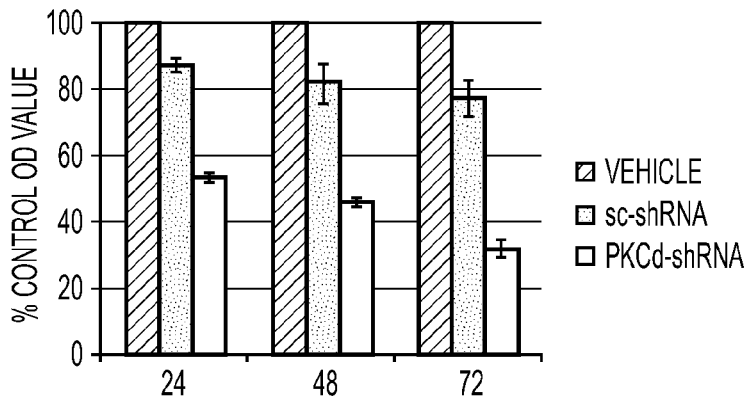
FIGS. 2A-2D. Effects of PKC delta knockdown by PKC delta-specific shRNA lentivirus on proliferation of human neuroendocrine tumor cells. BON1 (FIG. 2A), CNDT 2.5 (FIG. 2B) and H727 (FIG. 2C) cells were grown to 50% confluence in 96-well plates and then infected with PKC delta-shRNA-Lentivirus or scrambled shRNA Lentivirus (vector). Cell exposed to mock lentiviral infection (vehicle) also served as controls. After 24, 48, and 72 hours of treatment, cell proliferation was evaluated by MTS assay. Control values were normalized to 100%. Error bars represent SEM. P values for comparison between control (scrambled shRNA) lentivirus and PKC delta-shRNA lentivirus effects on cell number reached significance at 24 hr of exposure (p≤0.001) for all cell lines, and remained significant at the 48 and 72 hr time points.
Figure 2B:
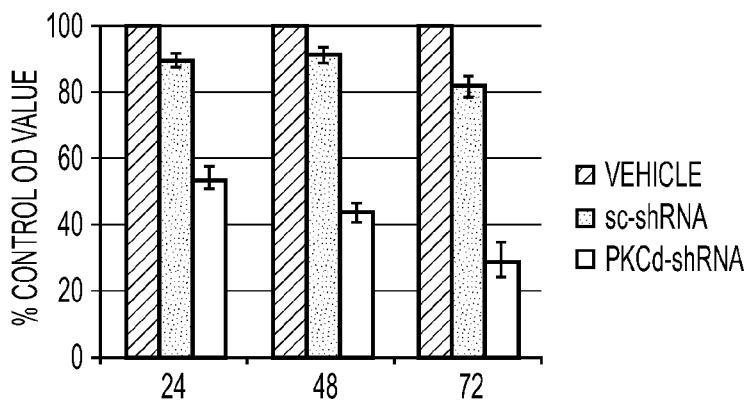
Figure 2C:
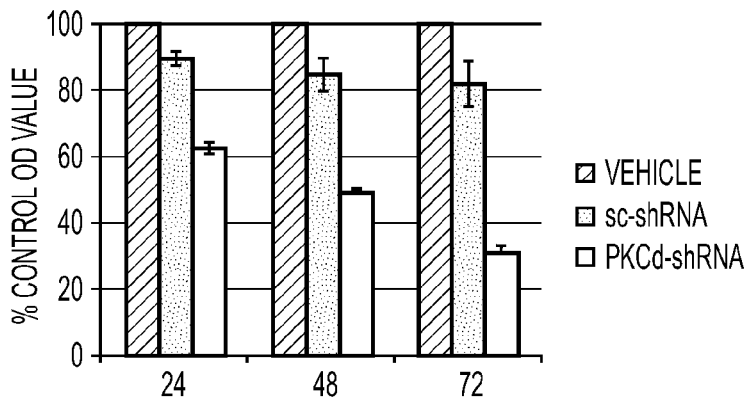
Figure 2D:
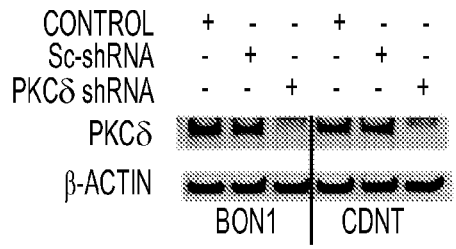

To confirm and extend these experiments, lentiviral vectors containing the same shRNA sequences (PKC delta-specific or scrambled) were constructed. Infection of the BON1, H727 and CNDT cell lines cell lines with these vectors demonstrated PKC delta-specific inhibition of proliferation (FIG. 2A-C). The lentiviral vector containing the scrambled sequence (control) consistently had a modest inhibitory effect on proliferation of both cell lines, but this never reached statistical significance. Efficient knockdown of PKC delta protein by specific siRNA was verified by immunoblotting.

Figure 3A:
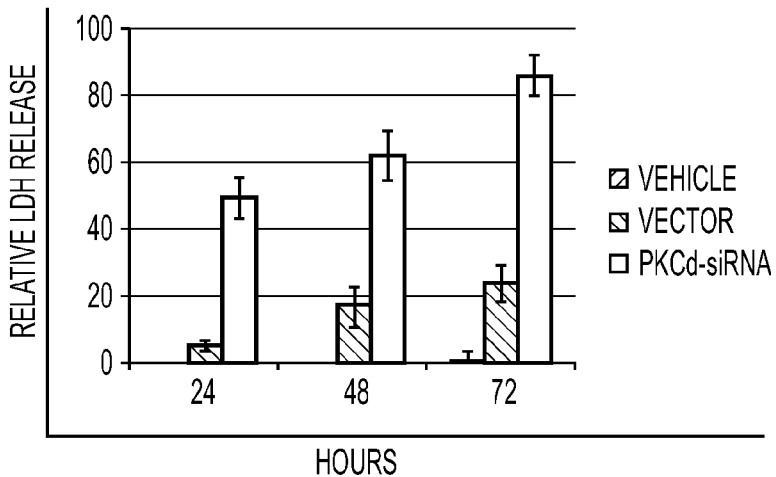
FIGS. 3A-3C. Cytotoxic effects of PKC delta knockdown by shRNA-lentivirus on human neuroendocrine tumor cell lines. BON1 (FIG. 3A), CNDT 2.5 (FIG. 3B) and H727 (FIG. 3C) cells were grown to 50% confluence in 96-well plates and then infected with PKC delta-shRNA-lentivirus or scrambled siRNA lentivirus (vector). Cell exposed to mock lentiviral infection (vehicle) also served as controls. After 24, 48 and 72 hours of treatment, cell cytotoxicity was evaluated by LDH-release assay. Total maximal LDH release is assigned the arbitrary value of 100%. Error bars represent SEM. P values for comparison between control (scrambled shRNA) lentivirus and PKCdelta-shRNA lentivirus effects on LDH release reached significance at 24 hr of exposure (p≤0.004) for all cell lines, and remained significant at the 48 and 72 hr time points.
Figure 3B:
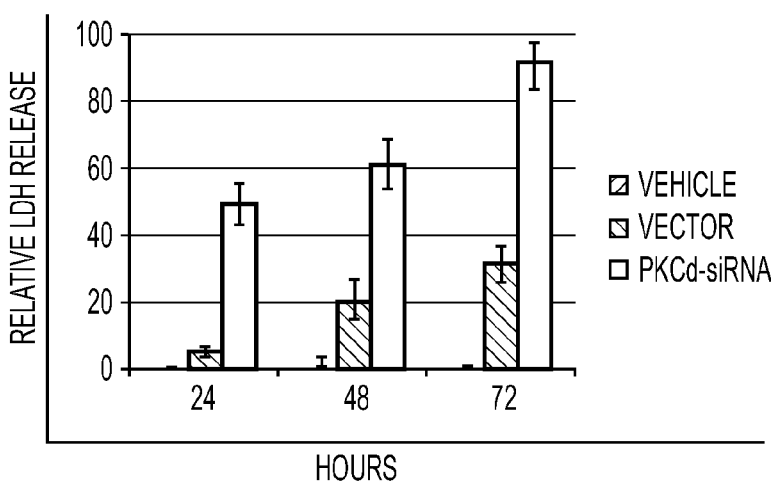
Figure 3C:
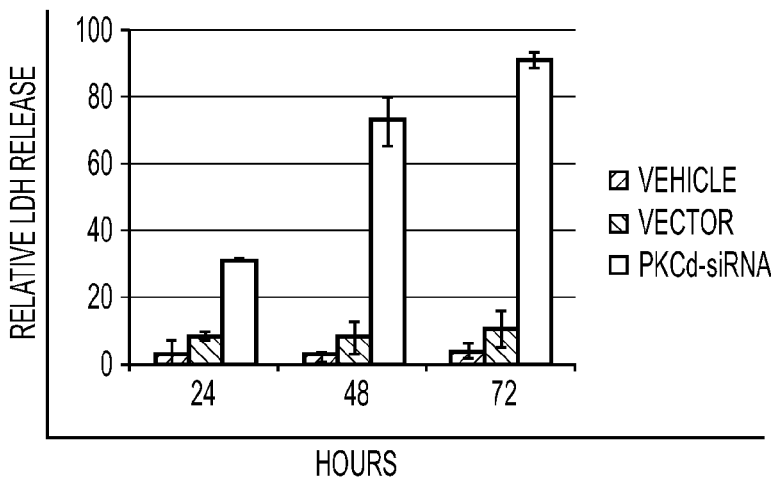

To determine if the inhibition of tumor cell proliferation by PKC delta knockdown was accompanied by cytotoxic effects on the tumor cells, cytotoxicity in these cell lines was evaluated by quantitating LDH release. Lactose dehydrogenase (LDH), a stable cytoplasmic enzyme, is rapidly released into the cell culture medium after damage of the plasma membrane, and its level correlates quantitatively with the extent of cytotoxicity. Significant increases in LDH release I cytotoxicity were detected within 24 hr of exposure to the lentiviral vector containing the PKC delta shRNA, and this release increased to approach the maximum possible LDH release (complete cell lysis, positive control) by 72 hr (FIG. 3A-C). Only modest, but detectable, increases in LDH release were induced by the control lentiviral vector.

Example 2

Small Molecule Inhibitors of PKC Delta are Cytotoxic to Neuroendocrine Tumor Cell Lines We next determined whether a series of small-molecule PKC delta inhibitors would inhibit the growth of human neuroendocrine tumor cell lines. While not as specific for the PKC delta isozyme as technology employing genetic knockdown of the PKC delta mRNA and protein, such small-molecule inhibitors are more relevant for eventual therapeutic application.

Figure 4:
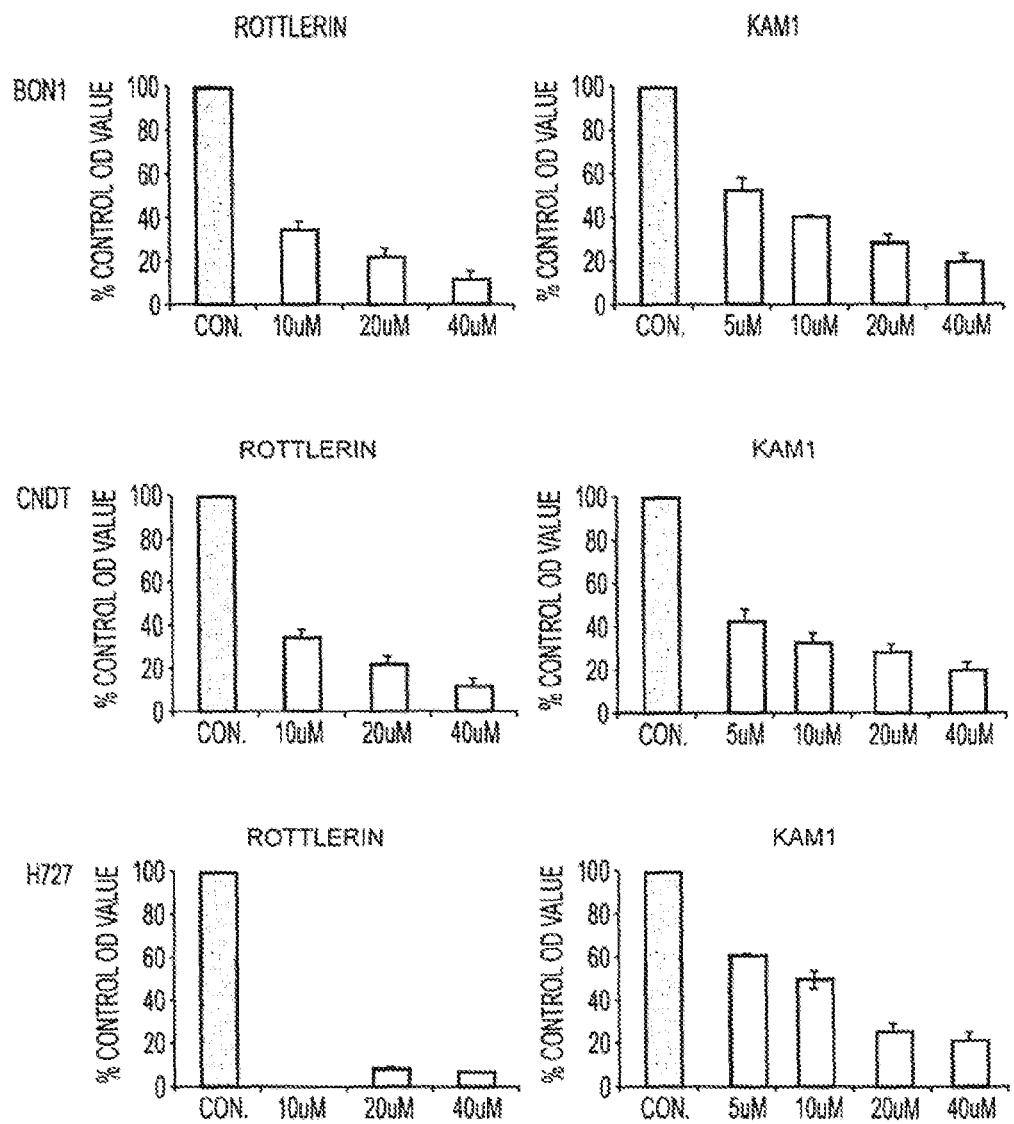
FIG. 4. Effects of PKC delta inhibitors on proliferation of human neuroendocrine tumor cell lines. Cells were grown to 80% confluence in 96-well plates and then treated with vehicle control (DMSO), rottlerin or KAM1 at 5, 10, 20 or 40 µM. The corresponding equivalent volumes of solvent were used as vehicle controls. After 72 hours of treatment, cell growth was evaluated by MTT assay. Control values were normalized to 100%. P values for comparison between control (vehicle) and rottlerin effects on cell number reached significance at 24 hr of exposure (p <0.004) for all cell lines, and remained significant at the 48 and 72 hr time points. P values for comparison between control (vehicle) and KAM1 effects on cell number reached significance by 72 hr of exposure (p<0.02) for all cell lines.
Figure 7A:
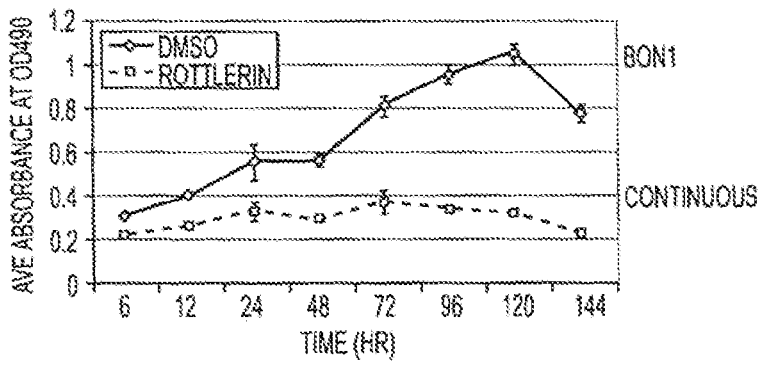
FIG. 7. Longer term exposure of human neuroendocrine tumor cell lines to PKC delta-inhibitors. BON1 cells (Panels A and C) or CNDT cells panels B and D) were exposed to rottlerin at a sub-optimal concentration (10 µM). Cells exposed to vehicle alone served as controls. At the indicated time points, cell numbers were estimated by MTS assays. In cultures depicted in panels A and B, media was not changed. In cultures depicted in panels C and D, fresh media containing the PKC delta inhibitor was replaced after 72 hr of exposure (arrows). Error bars represent SEM. (Fall off in cell numbers in control cultures at the longest time points likely reflect overgrowth observed in the control cultures.)
Figure 7B:
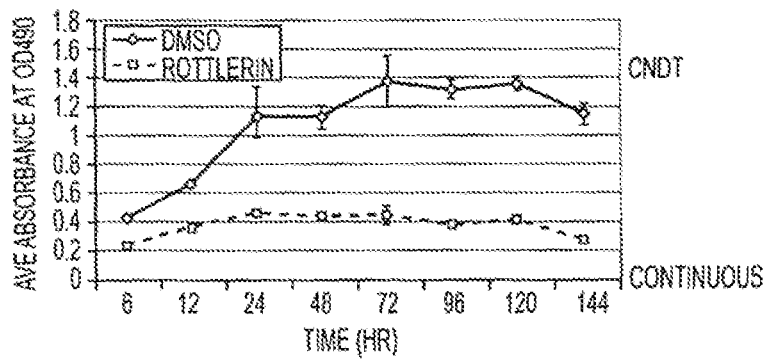
Figure 7C:
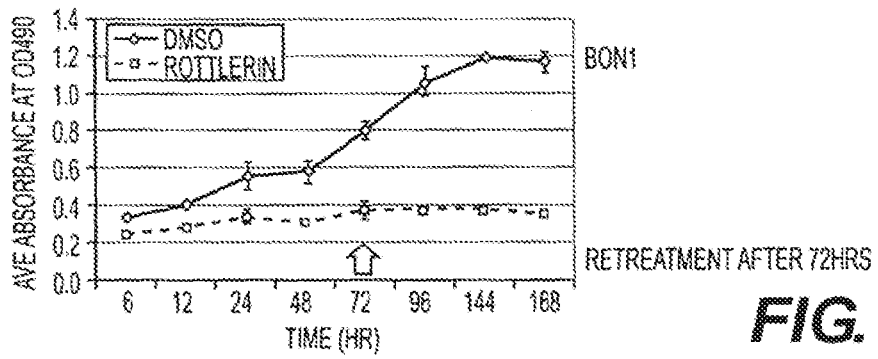
Figure 7D:
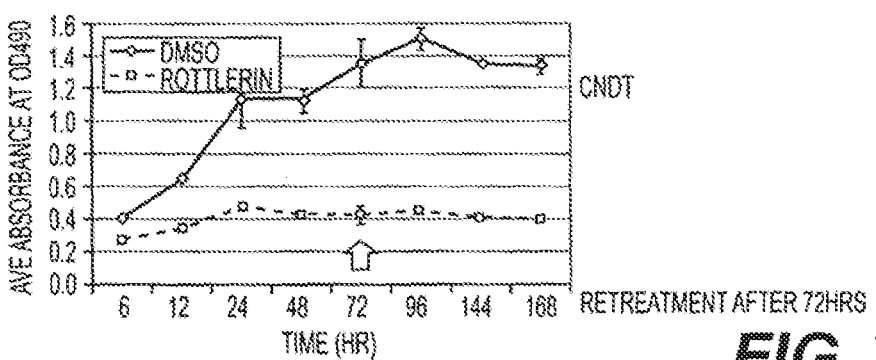

Rottlerin is a naturally-occurring product which inhibits purified PKC delta at an $IC_{50}$ of 1-3 mM in vitro, and inhibits PKC delta in cultured cells with an $IC_{50}$ of 5 µM in vivo. It is relatively selective for PKC delta (PKC delta/PKC alpha ($IC_{50}$:$IC_{50}$ is >1:30) (Gschwendt et al. 1994; Kikkawa et al. 2002), and confirmed in our in vitro assays (not shown). Furthermore, this compound not only directly inhibits purified PKC delta, but also, over longer periods of exposure, significantly down-regulates PKC delta protein specifically in cells, while having no effect on the levels of other PKC isozymes (Xia et al. 2007). Exposure to rottlerin produced a dose- and time-dependent decrease in cell number in the BON1, the CNDT 2.5, and the H727 cell lines, with an $IC_{50}$ of approximately 5 M by 48 hrs (not shown), and a significant reduction in relative cell numbers by 72 hrs at the highest concentrations tested (FIG. 4). In contrast, we have previously demonstrated that exposure to rottlerin under these same culture conditions has no significant effect on the growth of non-tumorigenic murine or human cells in culture (Xia et al. 2007).

Docking studies were conducted to predict how rottlerin binds to PKC delta. Rottlerin was docked into the catalytic binding site of several different PKC crystal structures. The structure of PKC θ complexed with staurosporine (pdb code 1XJD) was selected as the most suitable model. It is known from crystal structures of many kinase/inhibitor complexes that the kinase active site is flexible, therefore, regions known to be flexible were allowed to be free during the docking procedures. Chimeric molecules were designed using the PKC delta model developed from the rottlerin docking studies. The strategy was to retain most of the chromene part of rottlerin, which is assumed to give rottlerin its specificity but to vary the "head group" which is assumed to bind to the hinge region of the kinase active site. A novel PKC delta inhibitor, KAM1, which is a chimeric molecule containing the substituted chromene portion of rottlerin and the N-alkylated carbazole portion of staurosporine (a non-selective pan-PKC inhibitor) (FIG. 5), was next tested for cytotoxic effects on neuroendocrine tumor cells. Comparative analyses of PKC delta inhibitory activity showed an $IC_{50}$ of 0.2 mM for rottlerin and an $IC_{50}$ of 0.9 µM for KAM1. In contrast, the PKC alpha $IC_{50}$ was greater than 50 µM for each compound, demonstrating some specificity for the novel isozyme PKC delta over classic isozyme PKC alpha. KAM1 produced a dose- and time-dependent decrease in cell number in the BON1, the CNDT 2.5, and the H727 cell lines, with an $IC_{50}$ of approximately 12 µM by 48 hrs (not shown), and an 80% reduction in cell numbers by 72 hrs at the highest concentrations tested (FIGS. 4A&B).

In parallel, cytotoxicity, as assessed by LDH release, was induced by exposure of the H727 cells to rottlerin, with cytotoxicity increasing as a function of time and concentration of this inhibitor (FIG. 6).

Whether neuroendocrine tumor cell lines could escape from the anti-tumor actions of PKC inhibitors was explored by long-term exposure to the inhibitors, in two experimental designs. In the first, cells were plated at a lower density to allow monitoring over longer periods for potential growth. In these "continuous" treatment studies, a PKC delta inhibitor was added at a "suboptimal" concentration, and effects on proliferation were observed as far as 144 hr after exposure (FIGS. 7 A&B). The decrease observed in the MTS signal from the control (vehicle-treated) cells at 144 hr represented both overgrowth of these cultures and exhaustion of the culture media. To allow evaluation over even longer periods of exposure, other cultures were re-fed with fresh growth medium containing the same PKC delta inhibitor at the same concentration. In these studies, growth-inhibitory effects persisted to 168 hr of cumulative exposure (FIGS. 7 C&D).

Figure 8:
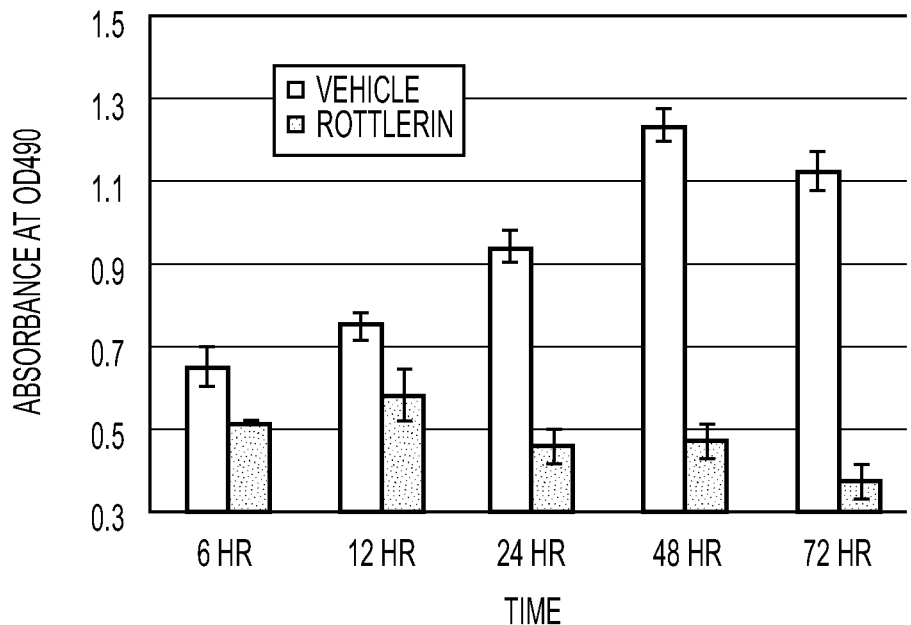
FIG. 8. Duration of exposure to PKC delta inhibitors needed to inhibit tumor cell proliferation. BON1 cells were grown to 30% confluence and then treated with vehicle as control (vehicle), or rottlerin at 10 uM, for 6, 12, 24, 48 or 72 hr. Media without inhibitor was replaced and cell numbers were estimated by MTS assay at 24, 48 and 72 hr. Shown here are the results at 72 hr of culture after each washout interval. Error bars represent SEM. Differences in proliferation between rottlerin- and vehicle-treated cultures became statistically significant by 24 hr of exposure, and remained significant for all longer periods of exposure.

The length of exposure to PKC delta inhibition required for anti-tumor activity was next assessed. neuroendocrine tumor lines were exposed to a sub-optimal concentration of a PKC delta-inhibitor for different intervals of time, the inhibitor was then washed out of the culture, and the effects on cell growth were assessed over the next 72 hrs. Differences in proliferation between rottlerin- and vehicle-treated cultures became statistically significant by 24 hr of exposure, and remained significant for all longer periods of exposure (FIG. 8).

Figure 9:
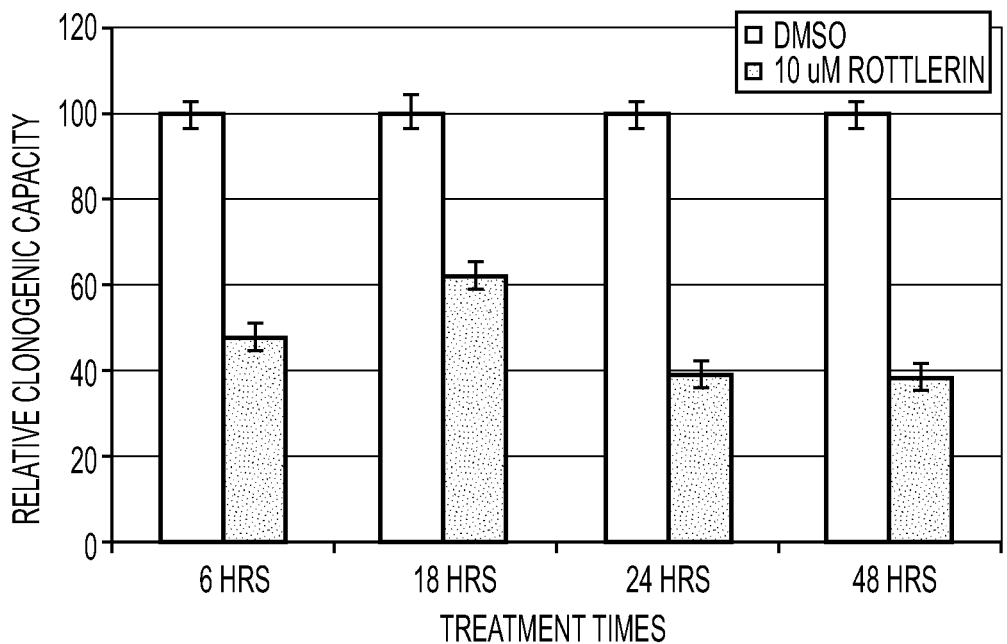
FIG. 9. Effects of PKC delta inhibitor on tumor cell clonogenic capacity H727 cells were grown to 30% confluence and then treated with vehicle as control (vehicle), or rottlerin at 10 µM, for 6, 12, 24, 48 or 72 hr. Viable cells were enumerated and re-plated in media without inhibitor, and colony numbers were quantitated 96 hr later. Error bars represent SEM. P value for comparison of DMSO control and rottlerin effects on clonogenic capacity reached significance (p=0.0051) at 6 hr of exposure and remained significant for all subsequent exposure times.

LDH release assesses cytotoxic damage sufficient to compromise membrane integrity over a relatively short time-span. An alternative method, which assesses lethal, but not necessarily immediate, cumulative damage to the tumor cell is a clonogenic assay. In this assay, tumor cells which remain viable after exposure to the compound are tested for their ability to proliferate sufficiently over time to form colonies of tumor cells. H727 treated with vehicle or a PKC delta inhibitor at sub-optimal concentrations varying durations. After re-plating of viable cells in media without inhibitor, colony numbers were quantitated over time. Significant effects of the PKC delta-inhibitors on effects on reducing clonogenic capacity reached significance after as little as 6 hr of exposure, and remained significant for all subsequent exposure times (FIG. 9). BON1 cells showed a similar drop-off in clonogenic capacity, reaching significance between 12 and 24 hr of exposure to PKC delta inhibitors.

Example 3

Ras Signaling in Neuroendocrine Tumor Cell Lines

Figure 10A:
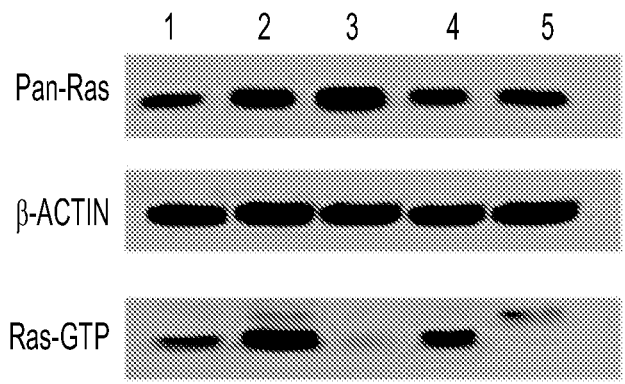
FIGS. 10A-10B. Ras signaling in neuroendocrine tumor cell lines.

Because of their sensitivity to PKC delta inhibition and "Ras-mediated apoptosis", the activity of p21Ras in these neuroendocrine tumor cell lines was assessed by affinity pull-down of GTP-bound p21Ras species. Endogenous Ras activity was high in the H727 cells, was only modestly elevated BON1 cells, and was not evident in the CNDT line, which contained GTP-bound p21Ras levels comparable to those found in non-transformed cells (FIG. 10A).

Figure 10B:
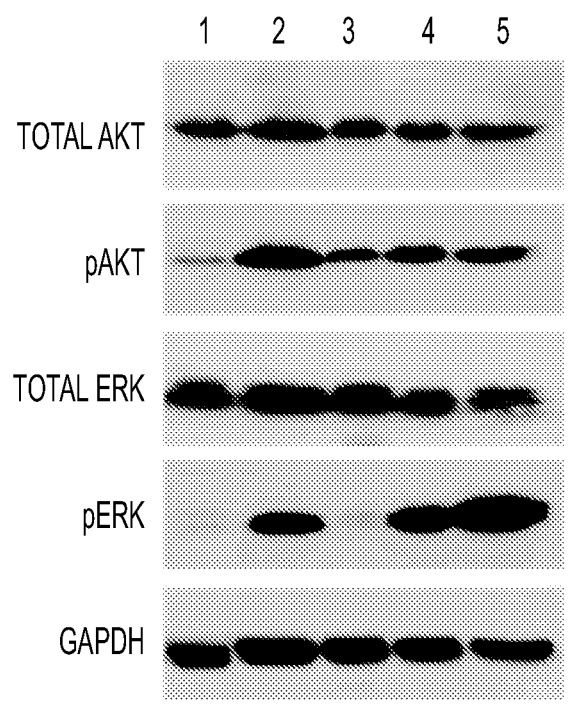
Figure 11A:
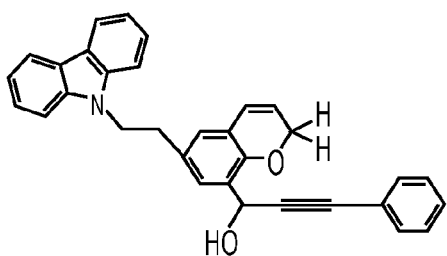
FIGS. 11A-11M show preferential embodiments of compounds for the methods and composition of the invention.
Figure 11B:
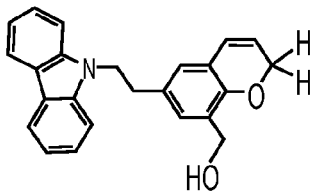
Figure 11C:
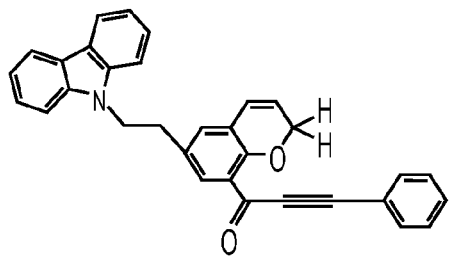
Figure 11D:
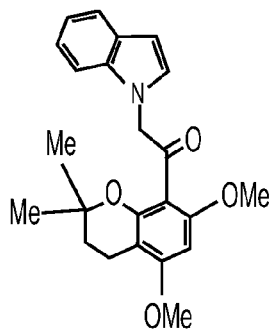
Figure 11E:
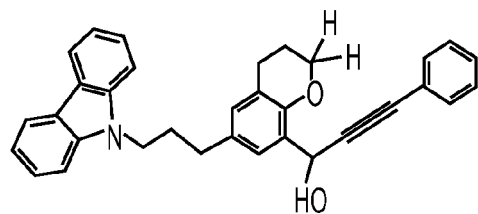
Figure 11F:
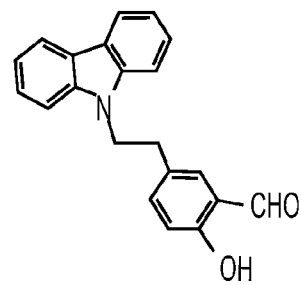
Figure 11G:
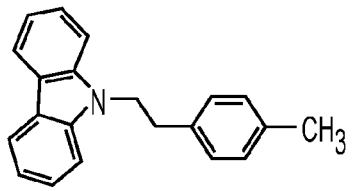
Figure 11H:
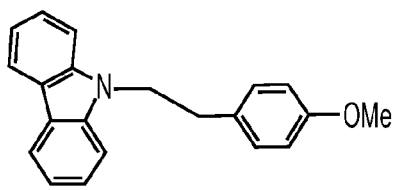
Figure 11I:
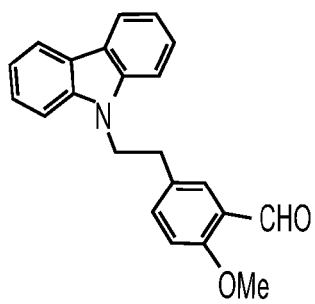
Figure 11J:
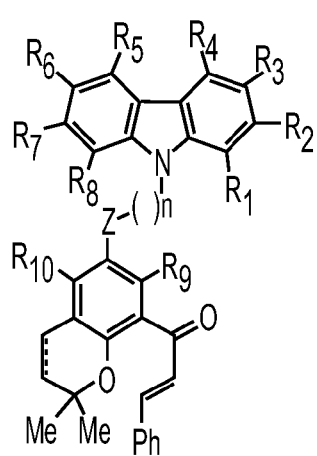
Figure 11K:
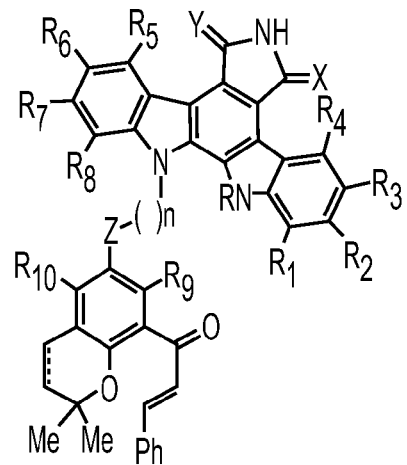
Figure 11L:
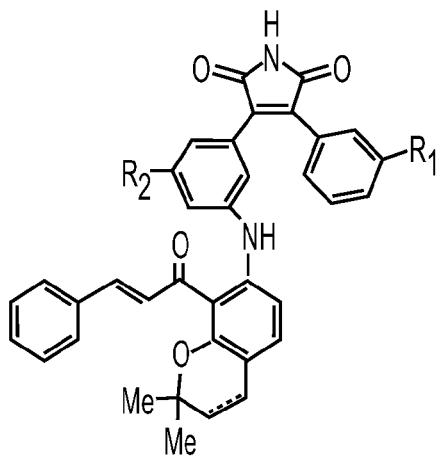
Figure 11M:
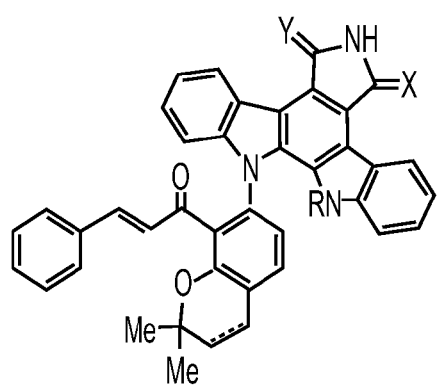

It has been previously demonstrated that aberrant activation of certain Ras signaling pathways, including the PI$_3$K-AKT pathway or the Raf-MAPK pathway, are sufficient to render tumor cells susceptible to PKC delta inhibition (Xia et al. 2007). The activation status of downstream elements of these signaling pathways was therefore explored in these neuroendocrine tumor cell lines. Evidence for activation of MAPK, as defined by relative elevation of phospho-ERK levels, was observed in the H727 and CNDT lines (compared to the non-transformed negative-control cell line MCF10) (FIG. 10B). Evidence for some activation of PI$_3$K, relative to the non-transformed negative control cell line MCF10, as defined by activating phosphorylation of AKT (Ser473), was observed in all three neuroendocrine tumor cell lines.

Example 4

Figure 12E:
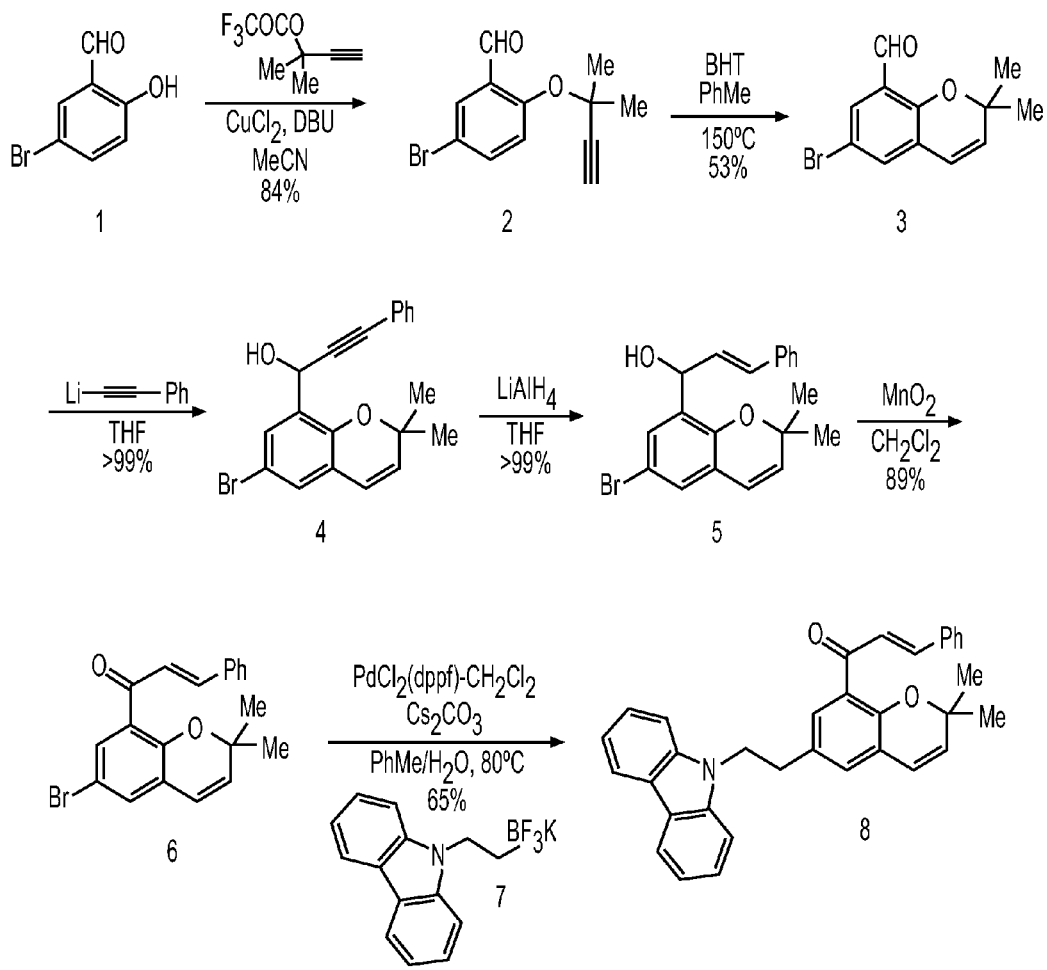
FIG. 12E shows a synthetic scheme for one embodiment of the invention.

Exemplary Synthesis. These examples are for illustration only and one of ordinary skill in the art would know how to modify the synthetic sequence to obtain the same or different compounds of the invention (see FIG. 12E).

Unless otherwise noted, all reagents were obtained from commercial suppliers and were used without further purification. All air or moisture sensitive reactions were performed under a positive pressured of argon in flame-dried glassware. Tetrahydrofuran (THF), toluene, diethyl ether (Et$_2$O), dichloromethane, benzene (PhH), acetonitrile (MeCN), triethylamine (NEt$_3$), pyridine, diisopropyl amine, methanol (MeOH), dimethylsulfoxide (DMSO), and N,N-dimethylformamide (DMF) were obtained from a dry solvent system (Ar degassed solvents delivered through activated alumina columns, positive pressure of argon). Column chromatography was performed on Merck silica gel Kieselgel 60 (230-400 mesh). $^1$HNMR and $^{13}$CNMR spectra were recorded on Varian 300, or 400 MHz spectrometers. Chemical shifts are reported in ppm relative to CHCl$_3$ at δ 7.27 ($^1$HNMR) and δ 77.23 ($^{13}$CNMR). Mass spectra were obtained on Fisons VG Autospec. IR spectra were obtained from thin films on a NaCl plate using a Perkin-Elmer 1600 series FT-IR spectrometer. See Compound 2, FIG. 12 F.

Synthesis of 6-bromo-2,2-dimethyl-2H-chromene-8-carbaldehyde (2): To a 100 mL flame dried round bottomed flask containing 5.54 mL (57.2 mmol, 1.15 equiv) 2-methylbut-3-yn-2-ol dissolved in 50 mL dry MeCN at 0° C. was added 11.1 mL (74.6 mmol, 1.5 equiv.) DBU followed by the dropwise addition of 8.08 mL (57.2 mmol, 1.15 equiv.) freshly distilled TFAA. The reaction was stirred at 0° C. for 30 min before being added via cannula to a 250 mL round bottomed flask containing 10.0 g (49.7 mmol, 1 equiv.) 5-bromo-2-hydroxybenzaldehyde, 9.65 mL (64.6 mmol, 1.3 equiv.) DBU, and 8.5 mg (0.050 mmol, 0.001 equiv.) CuCh-2H$_2$O dissolved in dry MeCN at −5° C. The reaction was stirred for 16 hr at ambient temperature before being concentrated under reduced pressure. The resulting residue was taken up in EtOAc, washed once with H$_2$O, once with 1 M HCl, and once with brine before being dried over Na$_2$SO$_4$, and concentrated. This residue was subjected to silica gel flash chromatography eluting with 19:1 to 4:1 hex/EtOAc to yield 11.17 g (84%) of the desired product (2) as a pale yellow solid. See Compound 3, FIG. 12F.

$^1$HNMR (300 MHz, CDCl$_3$) δ 10.27 (s, 1H), 7.88 (s, 1H), 7.55 (d, J=8.4, 1H), 7.38 (d, J=8.4, 1H), 2.63 (s, 1H), 1.67 (s, 6H);); $^{13}$CNMR (75 MHz, CDCl$_2$) 6 188.8, 157.4, 137.5, 130.9, 130.2, 122.8, 116.1, 84.7, 76.3, 74.5, 29.7; IR (NaCl, film) 3294, 1687, 1588, 1471 cm$^{-1}$; HRMS (+TOF) 267.0015 calcd for C$_{12}$H$_{12}$BrO$_2$ [M+H]$^+$, found: 267.0016; R$_f$=0.38 (9:1 hex./EtOAc).

Synthesis of 6-bromo-2,2-dimethyl-2H-chromene-8-carbaldehyde (3): To an 80 mL microwave reaction vessel containing 4.00 g (14.8 mmol, 1 equiv.) 5-bromo-2-((2-methylbut-3-yn-2-yl)oxy)benzaldehyde dissolved in 60 mL dry MeCN was added 66.0 mg (0.300 mmol, 0.02 equiv.) BHT. The reaction was heated in a microwave reactor to 180° C. for 20 min before being concentrated and purified by silica gel flash chromatography eluting with 19:1 hex./EtOAc to yield 2.10 g (53%) of the desired product (3) as a yellow oil. See Compound 4, FIG. 12F.

$^1$HNMR (300 MHz, CDCl$_3$) δ 10.35 (s, 1H), 7.73 (d, J=2.7, 1H), 7.27 (dd, J=2.7, 0.3, 1H), 6.29 (d, J=9.9, 1H), 5.75 (d,

J=9.9, 1H), 1.50 (s, 3H); $^{13}$CNMR (75 MHz, CDCl$_3$) δ 188.0, 155.3, 134.3, 132.8, 129.4, 125.6, 124.6, 120.8, 113.4, 78.4, 28.4; IR (NaCl, film) 2863, 1678, 1574 cm$^{-1}$; HRMS(+TOF) 267.0015 calcd for C$_{12}$H$_{12}$BrO$_2$ [M+H]$^+$, found: 267.0012; R$_f$=0.33 (9:1 hex./EtOAc).

Synthesis of 1-(6-bromo-2,2-dimethyl-2H-chromen-8-yl)-3-phenylprop-2-yn-1-ol (4): To a flame dried 100 mL round bottomed flask containing 745 mg (7.30 mmol, 1.3 equiv.) ethynylbenzene dissolved in 30 mL dry THF at −78° C. was dropwise added 4.2 mL (6.7 mmol, 1.2 equiv) of a 1.6 M solution of n-BuLi in hexanes. The reaction was allowed to stir at −78° C. for 30 min before the addition of 1.50 g (5.62 mmol, 1 equiv.) 6-bromo-2,2-dimethyl-2H-chromene-8-carbaldehyde dissolved in 10 mL dry THF. After stirring for 30 min at −78° C. the reaction was poured into saturated NH$_4$Cl$_{(aq)2}$, extracted into EtOAc, dried over Na$_2$SO$_4$, and concentrated. The resulting residue was purified by silica gel flash chromatography eluting with 4:1 hex./EtOAc yielding 2.1 g (99%) of the desired product (4) as a yellow oil. See Compound 5, FIG. 12F.

$^1$HNMR (300 MHz, CDCl$_3$) δ 7.52 (d, J=2.4, 1H), 7.46 (m, 2H), 7.33 (m, 3H), 7.10 (d, J=2.4. 1H), 6.27 (d, J=9.9, 1H), 5.78 (s, 1H), 5.69 (d, J=9.6, 1H), 3.06 (bs, 1H), 1.49 (s, 3H), 1.48 (s, 3H); $^{13}$CNMR (75 MHz, CDCl$_3$) δ 149.5, 132.2, 132.0, 130.3, 130.1, 129.1, 128.7, 128.5, 123.6, 122.7, 121.4, 113.1, 88.2, 86.3, 77.8, 61.3, 28.2, 28.2; IR (NaCl, film) 3428 br, 2230 cm$^4$; HRMS (+TOF) 351.0379 calcd. for C$_{20}$H$_{16}$BrO [M−H$_2$O]$^+$, found: 351.0389; R$_f$=0.40 (4:1 hex./EtOAc).

Synthesis of (E)-1-(6-bromo-2,2-dimethyl-2H-chromen-8-yl)-3-phenylprop-2-en-1-ol (5):

To a 10 mL round bottomed flask containing 100 mg (0.271 mmol, 1 equiv.) 1-(6-bromo-2,2-dimethyl-2H-chromen-8-yl)-3-phenylprop-2-yn-1-ol dissolved in 1.5 mL dry THF was added 12 mg (0.33 mmol, 1.2 equiv.) LiAlH4. The reaction was heated to reflux for 1 hr and cooled to ambient temperature. The reaction was quenched by addition of H$_2$O followed by 15% NaOH (aq.) and then EtOAc. The organic layer was separated and then filtered through a short silica gel plug before being concentrated to yield 100 mg (99%) of the desired product (5) as a yellow oil. See Compound 6, FIG. 12F.

$^1$HNMR (300 MHz, CDCl$_3$) δ 7.40-7.24 (m, 6H), 7.06 (d, J=2.4, 1H), 6.70 (d, J=15.9, 1H), 6.38 (dd, J=15.9, 5.4, 1H), 6.26 (d, J=9.9, 1H), 5.66 (d, J=9.9, 1H), 5.50 (m, 1H), 1.44 (s, 3H), 1.42 (s, 3H); $^{13}$CNMR (75 MHz, CDCb) δ149.0, 136.9, 132.5, 132.0, 130.6, 129.5, 128.8, 128.8, 128.3, 127.9, 126.8, 123.5, 121.6, 113.3, 77.4, 70.7, 28.3, 28.2; IR (NaCl, film) 3416 br cm$^{-1}$; HRMS (+TOF) 353.0536 calcd for C$_{11}$H$_{15}$O$_3$ [M−H$_2$O]$^+$, found: 353.0548; R$_f$=0.26 (9:1 hex./EtOAc).

Synthesis of (E)-1-(6-bromo-2,2-dimethyl-2H-chromen-8-yl)-3-phenylprop-2-en-1-one (6): To a 50 ml round bottomed flask containing 1.41 g (3.80 mmol, 1 equiv.) (E)-1-(6-bromo-2,2-dimethyl-2H-chromen-8-yl)-3-phenylprop-2-en-1-ol dissolved in 20 mL dry CH2Ch was added 1.98 g (22.8 mmol, 6 equiv.) MnO$_2$ and the reaction was stirred at ambient temperature for 2 hr. The reaction was filtered through celite and concentrated. The resulting residue was purified by silica gel flash chromatography eluting with 19:1 to 4:1 hex./EtOAc yielding 1.25 g (89%) of the desired product (6) as a yellow oil. See Compound 8, FIG. 12F.

$^1$HNMR (300 MHz, CDCl$_3$) δ 7.70-7.39 (m, 8H), 7.22 (d, J=2.4, 1H), 6.31 (d, J=9.9, 1H), 5.72 (d, J=9.9, 1H), 1.49 (s, 6H); $^{13}$CNMR (75 MHz, CDCl$_3$) δ 190.6, 151.3, 143.4, 135.3, 132.3, 130.6, 129.8, 129.2, 128.7, 128.5, 126.7, 124.2, 121.4, 113.2, 78.0, 28.5; IR (NaCl, film) 1654, 1603, 1435 cm$^{-1}$; HRMS (+TOP) 369.0485 calcd for C$_{20}$H$_{18}$BrO$_2$ [M+H]$^+$, found: 369.0489; R$_f$=0.50 (4:1 hex./EtOAc).

Synthesis of Compound 8 (KAM-1): To a 10 mL round bottomed flask containing 92 mg (0.25 mmol, 1 equiv.) (E)-1-(6-bromo-2,2-dimethyl-2H-chromen-8-yl)-3-phenylprop-2-en-1-one and 83 mg (0.28 mmol, 1.1 equiv.) of Molander salt XX was added 9 mg (0.012 mmol, 0.05 equiv.) PdCb(dppf)-CH$_2$Ch and 245 mg (0.75 mmol, 3 equiv.) Cs$_2$CO$_3$ followed by 1.5 mL dry PhMe and 0.5 mL H$_2$O. The reaction was heated to 80° C. for 12 hr, filtered through cotton and concentrated. Purification by silica gel flash chromatography eluting with 9:1 hex./EtOAc yielded 78 mg (65%) of the desired product (8) as a yellow oil.

$^1$HNMR (300 MHz, CDCl$_3$) δ 8.10 (d, J=7.5, 2H), 7.71-7.20 (m, 14H), 6.76 (d, J=2.4, 1H), 6.21 (d, J=9.9, 1H), 5.65 (d, J=9.9, 1H), 4.51 (t, J=7.8, 2H), 3.06 (t, J=7.8, 2H), 1.48 (s, 6H). $^{13}$CNMR (75 MHz, CDCl$_3$): δ 191.9, 151.3, 142.6, 140.3, 135.6, 131.3, 131.1, 130.8, 130.4, 130.1, 129.2, 128.5, 128.3, 127.2, 125.8, 123.1, 122.5, 122.2, 120.6, 119.1, 108.8, 44.9, 34.3, 28.4. IR (NaCl, film) 1655, 1596, 1485, 1453 cm$^{-1}$. HRMS (+TOF) 484.2271 calcd for C$_{34}$H$_{30}$NO$_2$ [M+H]$^+$, found: 484.2269; R$_f$=0.21 (9:1 hex./EtOAc).

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A compound of the formula:

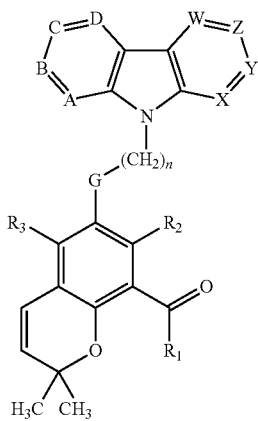

wherein:
 $R_1$ is selected from the group consisting of H and a lower alkyl;
 $R_2$ and $R_3$ are each independently selected from the group consisting of H, OH and OR;
 A, B, C, D, W, X, Y, and Z are each independently selected from the group consisting of N and CH;
 G is selected from the group consisting of O, NR, S, and $CH_2$,
 R is selected from the group consisting of H, a lower alkyl and aryl; and
 n is an integer selected from the group consisting of 1, 2, 3, and 4;
 or a pharmaceutically acceptable salt thereof.

2. The compound of claim 1, wherein $R_1$ is H.

3. The compound of claim 1, wherein $R_2$ and $R_3$ are each independently H or OR, and OR is OH or $OCH_3$.

4. The compound of claim 1, wherein $R_2$ and $R_3$ are each H.

5. The compound of claim 1, wherein A, B, C, D, W, X, Y, and Z are each CH.

6. The compound of claim 1, wherein G is $CH_2$.

7. The compound of claim 1, wherein n is 1.

8. The compound of claim 1, wherein n is 2.

9. The compound of claim 1, wherein the pharmaceutically acceptable salt is selected from the group consisting of ammonium, calcium, sodium, and combinations thereof.

10. A compound of the formula;

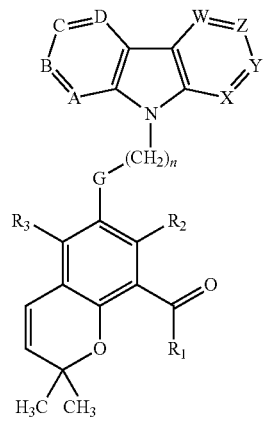

wherein:
 $R_1$ is H;
 $R_2$ and $R_3$ are each H;
 A, B, C, D, W, X, Y, and Z are each CH; and
 G is $CH_2$; and n is an integer selected from the group consisting of 1, 2, 3 and 4; or a pharmaceutically acceptable salt thereof.

11. The compound of claim 10, wherein n is 1.

12. The compound of claim 10, wherein n is 2.

13. The compound of claim 10, in the form of a pharmaceutically acceptable salt.

14. The compound of claim 13, wherein the pharmaceutically acceptable salt is selected from the group consisting of ammonium, calcium, sodium, and combinations thereof.

15. A compound of the formula:

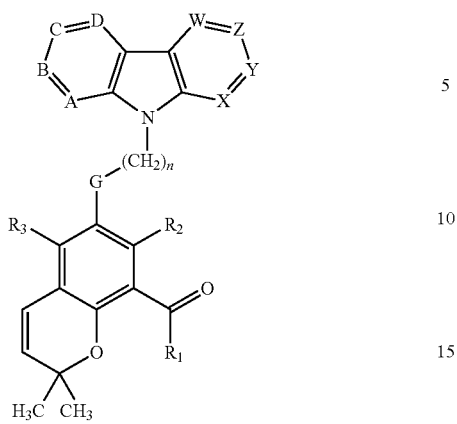

wherein:
$R_1$ is H;
$R_2$ is H;
$R_3$ is $OCH_3$;
A, B, C, D, W, X, Y, and Z are each CH;
G is $CH_2$; and
n is 1; or a pharmaceutically acceptable salt thereof.

16. The compound of claim 15, in the form of a pharmaceutically acceptable salt.

17. The compound of claim 16 wherein the pharmaceutically acceptable salt is selected from the group consisting of ammonium, calcium, sodium, and combinations thereof.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

```
<223> OTHER INFORMATION: Description of Combined DNA/RNA Molecule:
      Synthetic oligonucleotide

<400> SEQUENCE: 1
gaugaaggag gcgcucagtt                                               20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
ggcugaguuc uggcuggact t                                             21
```